US008704855B1

(12) United States Patent
Berme et al.

(10) Patent No.: US 8,704,855 B1
(45) Date of Patent: Apr. 22, 2014

(54) FORCE MEASUREMENT SYSTEM HAVING A DISPLACEABLE FORCE MEASUREMENT ASSEMBLY

(71) Applicant: Bertec Corporation, Columbus, OH (US)

(72) Inventors: Necip Berme, Worthington, OH (US); Scott Zerkle Barnes, Thornville, OH (US); Lewis Michael Nashner, Watertown, MA (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 13/904,751

(22) Filed: May 29, 2013

Related U.S. Application Data

(60) Provisional application No. 61/754,556, filed on Jan. 19, 2013.

(51) Int. Cl.
G09G 5/12 (2006.01)
(52) U.S. Cl.
USPC .......................................... 345/633
(58) Field of Classification Search
USPC .......................................... 345/633
See application file for complete search history.

(56) References Cited

U.S. PATENT DOCUMENTS

| 4,009,607 | A | * | 3/1977 | Ficken ..................... 73/862.61 |
| 4,489,932 | A | | 12/1984 | Young |
| 4,738,269 | A | | 4/1988 | Nashner |
| 4,830,024 | A | | 5/1989 | Nashner et al. |
| 5,052,406 | A | | 10/1991 | Nashner |
| 5,269,318 | A | | 12/1993 | Nashner |
| 5,303,715 | A | | 4/1994 | Nashner et al. |
| 5,366,375 | A | * | 11/1994 | Sarnicola ..................... 434/37 |
| 5,429,140 | A | * | 7/1995 | Burdea et al. ................ 600/587 |
| 5,474,087 | A | | 12/1995 | Nashner |
| 5,476,103 | A | | 12/1995 | Nahsner |
| 5,490,784 | A | | 2/1996 | Carmein |
| 5,551,445 | A | | 9/1996 | Nashner |
| 5,623,944 | A | | 4/1997 | Nashner |
| 5,697,791 | A | | 12/1997 | Nashner et al. |
| 5,745,126 | A | * | 4/1998 | Jain et al. ..................... 382/154 |

(Continued)

OTHER PUBLICATIONS

"Standing, walking, running, and jumping on a force plate" Rod Cross, Am. J. Phys. 67 (4), Apr. 1999.*

(Continued)

Primary Examiner — Javid A Amini
(74) Attorney, Agent, or Firm — The Law Office of Patrick F. O'Reilly III, LLC

(57) ABSTRACT

A force measurement system having a displaceable force measurement assembly includes: a force measurement assembly with a surface configured to receive a subject, and having at least one force transducer; at least one actuator operatively coupled to the force measurement assembly, the at least one actuator configured to displace the force measurement assembly; at least one visual display device having an output screen, the at least one visual display device configured to display one or more virtual reality scenes on the output screen so as to create a simulated environment for the subject; and one or more data processing devices operatively coupled to the force measurement assembly, the at least one actuator, and the at least one visual display device. In one or more embodiments, a method for testing a subject disposed on a displaceable force measurement assembly is further disclosed.

21 Claims, 17 Drawing Sheets

(56) References Cited

U.S. PATENT DOCUMENTS

| | | | |
|---|---|---|---|
| 5,769,640 A * | 6/1998 | Jacobus et al. ................ 434/262 |
| 5,846,134 A * | 12/1998 | Latypov ........................ 463/46 |
| 5,980,256 A * | 11/1999 | Carmein ........................ 434/55 |
| 5,980,429 A | 11/1999 | Nashner |
| 6,010,465 A | 1/2000 | Nashner |
| 6,038,488 A | 3/2000 | Barnes et al. |
| 6,063,046 A | 5/2000 | Allum |
| 6,113,237 A | 9/2000 | Ober et al. |
| 6,152,564 A | 11/2000 | Ober et al. |
| 6,190,287 B1 | 2/2001 | Nashner |
| 6,289,299 B1 * | 9/2001 | Daniel et al. .................... 703/21 |
| 6,295,878 B1 | 10/2001 | Berme |
| 6,307,567 B1 * | 10/2001 | Cohen-Or .................... 345/619 |
| 6,354,155 B1 | 3/2002 | Berme |
| 6,389,883 B1 | 5/2002 | Berme et al. |
| 6,449,103 B1 | 9/2002 | Charles |
| 6,632,158 B1 | 10/2003 | Nashner |
| 6,704,694 B1 | 3/2004 | Basdogan et al. |
| 6,738,065 B1 | 5/2004 | Even-Zohar |
| 6,774,885 B1 | 8/2004 | Even-Zohar |
| 6,936,016 B2 | 8/2005 | Berme et al. |
| 7,127,376 B2 | 10/2006 | Nashner |
| 7,179,234 B2 | 2/2007 | Nashner |
| 7,195,355 B2 | 3/2007 | Nashner |
| RE40,427 E | 7/2008 | Nashner |
| 7,500,752 B2 | 3/2009 | Nashner |
| 7,761,269 B1 | 7/2010 | Kraal et al. |
| 7,780,573 B1 | 8/2010 | Carmein |
| 7,931,604 B2 | 4/2011 | Even-Zohar et al. |
| 8,181,541 B2 | 5/2012 | Berme |
| 8,296,858 B2 * | 10/2012 | Striegler et al. ................ 850/14 |
| 8,315,822 B2 | 11/2012 | Berme et al. |
| 8,315,823 B2 | 11/2012 | Berme et al. |
| RE44,396 E | 7/2013 | Roston et al. |
| 2002/0010571 A1 * | 1/2002 | Daniel et al. .................... 703/21 |
| 2003/0011561 A1 * | 1/2003 | Stewart et al. ................. 345/156 |
| 2003/0122872 A1 * | 7/2003 | Chiang et al. ................. 345/763 |
| 2003/0216656 A1 | 11/2003 | Berme et al. |
| 2003/0216895 A1 * | 11/2003 | Ghaboussi et al. ............... 703/2 |
| 2004/0027394 A1 * | 2/2004 | Schonberg .................... 345/850 |
| 2004/0127337 A1 | 7/2004 | Nashner |
| 2004/0216517 A1 * | 11/2004 | Xi et al. ........................ 73/105 |
| 2004/0227727 A1 * | 11/2004 | Schena et al. ................. 345/156 |
| 2005/0043661 A1 | 2/2005 | Nashner |
| 2005/0075833 A1 | 4/2005 | Nashner |
| 2005/0148432 A1 | 7/2005 | Carmein |
| 2005/0243277 A1 | 11/2005 | Nashner |
| 2006/0115348 A1 * | 6/2006 | Kramer ............................ 414/5 |
| 2006/0264786 A1 | 11/2006 | Nashner |
| 2007/0064311 A1 | 3/2007 | Park |
| 2007/0093989 A1 | 4/2007 | Nashner |
| 2007/0121066 A1 | 5/2007 | Nashner |
| 2007/0135265 A1 | 6/2007 | Nashner |
| 2008/0034383 A1 * | 2/2008 | Harwin et al. ................. 720/651 |
| 2008/0204666 A1 | 8/2008 | Spearman |
| 2008/0221487 A1 | 9/2008 | Zohar et al. |
| 2008/0228110 A1 | 9/2008 | Berme |
| 2009/0059096 A1 * | 3/2009 | Yamamoto et al. ........... 348/746 |
| 2009/0119030 A1 * | 5/2009 | Fang et al. ..................... 702/41 |
| 2009/0126096 A1 * | 5/2009 | Bocos ............................. 4/496 |
| 2009/0137933 A1 * | 5/2009 | Lieberman et al. ........... 600/595 |
| 2009/0325699 A1 | 12/2009 | Delgiannidis |
| 2010/0092267 A1 * | 4/2010 | Najdovski et al. ................ 414/7 |
| 2010/0097526 A1 | 4/2010 | Jacob |
| 2010/0131113 A1 | 5/2010 | Even-Zohar |
| 2010/0137064 A1 * | 6/2010 | Shum et al. ..................... 463/36 |
| 2010/0176952 A1 * | 7/2010 | Bajcsy et al. ............... 340/573.1 |
| 2010/0197462 A1 * | 8/2010 | Piane, Jr. ......................... 482/5 |
| 2010/0302142 A1 * | 12/2010 | French et al. .................. 345/156 |
| 2011/0009241 A1 * | 1/2011 | Lane et al. ........................ 482/8 |
| 2011/0072367 A1 * | 3/2011 | Bauer ........................... 715/757 |
| 2011/0092882 A1 * | 4/2011 | Firlik et al. ..................... 604/20 |
| 2011/0115787 A1 | 5/2011 | Kadlec |
| 2011/0237396 A1 * | 9/2011 | Lu ..................................... 482/1 |
| 2011/0256983 A1 * | 10/2011 | Malack et al. .................... 482/4 |
| 2011/0277562 A1 | 11/2011 | Berme |
| 2011/0300994 A1 * | 12/2011 | Verkaaik et al. ................ 482/51 |
| 2012/0013530 A1 * | 1/2012 | Tsuboi et al. .................. 345/157 |
| 2012/0065784 A1 * | 3/2012 | Feldman ....................... 700/280 |
| 2012/0108909 A1 * | 5/2012 | Slobounov et al. ........... 600/300 |
| 2012/0113209 A1 | 5/2012 | Ritchey et al. |
| 2012/0122062 A1 * | 5/2012 | Yang et al. .................... 434/219 |
| 2012/0176411 A1 | 7/2012 | Huston |
| 2012/0266648 A1 | 10/2012 | Berme et al. |
| 2012/0271565 A1 * | 10/2012 | Berme et al. ..................... 702/41 |
| 2012/0303332 A1 * | 11/2012 | Mangione-Smith ............. 703/1 |
| 2013/0005415 A1 * | 1/2013 | Thomas et al. ................... 463/4 |
| 2013/0012357 A1 * | 1/2013 | Wang ............................. 482/4 |
| 2013/0022947 A1 * | 1/2013 | Muniz Simas et al. ........ 434/236 |
| 2013/0033967 A1 * | 2/2013 | Chuang et al. ................ 367/140 |
| 2013/0050260 A1 * | 2/2013 | Reitan ........................... 345/633 |
| 2013/0117377 A1 * | 5/2013 | Miller ........................... 709/205 |
| 2013/0127980 A1 * | 5/2013 | Haddick et al. ............ 348/14.08 |
| 2013/0278631 A1 * | 10/2013 | Border et al. ................. 345/633 |

OTHER PUBLICATIONS

Dynamic Control of a Moving Platform using the CAREN System to Optimize Walking inVirtual Reality Environments; 31st Annual International Conference of the IEEE EMBS Minneapolis, Minnesota, USA, Sep. 2-6, 2009, by Hassan El Makssoud, Carol L. Richards, and François Comeau.*

U.S. Appl. No. 13/348,506, entitled "Force Measurement System Having a Plurality of Measurement Surfaces", Inventor: Dr. Necip Berme, filed Jan. 11, 2012.

BalanceCheck Screener—Protocol Guide, Bertec Corporation, Version 1.1.0, last updated Mar. 2012.

BalanceCheck Trainer—Protocol Guide, Bertec Corporation, Version 1.1.0, last updated Mar. 2012.

Gates et al., Journal of NeuroEngineering and Rehabilitation 2012, 9:81, "Comparison of walking overground and in a Computer Assisted Rehabilitation Environment (CAREN) in individuals with and without transtibial amputation".

Mark Fondren, Monica Foster, Mitch Johnson, Drew Parks, Adam Vaclavik, "Virtual Rehabilitation", http://engineeringworks.tamu.edu/2011/virtual-reality-for-high-tech-rehabilitation-2/; 2011.

First office action on the merits (Non-Final Rejection) in U.S. Appl. No. 13/958,348, mailed on Dec. 5, 2013.

* cited by examiner

FORCE MEASUREMENT SYSTEM HAVING A DISPLACEABLE FORCE MEASUREMENT ASSEMBLY

CROSS-REFERENCE TO RELATED APPLICATIONS

This patent application claims priority to, and incorporates by reference in its entirety, pending U.S. Provisional Patent Application No. 61/754,556, entitled "Force Measurement System Having A Displaceable Force Measurement Assembly", filed on Jan. 19, 2013.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a force measurement system. More particularly, the invention relates to a force measurement system having a displaceable force measurement assembly.

2. Background

Force measurement systems are utilized in various fields to quantify the reaction forces and moments exchanged between a body and support surface. For example, in biomedical applications, force measurement systems are used for gait analysis, assessing balance and mobility, evaluating sports performance, and assessing ergonomics. In order to quantify the forces and moments resulting from the body disposed thereon, the force measurement system includes some type of force measurement device. Depending on the particular application, the force measurement device may take the form of a balance plate, force plate, jump plate, an instrumented treadmill, or some other device that is capable of quantifying the forces and moments exchanged between the body and the support surface.

A balance assessment of a human subject is frequently performed using a specialized type of a force plate, which is generally known as a balance plate. In general, individuals maintain their balance using inputs from proprioceptive, vestibular and visual systems. Conventional balance systems are known that assess one or more of these inputs. However, these conventional balance systems often employ antiquated technology that significantly affects their ability to accurately assess a person's balance and/or renders them cumbersome and difficult to use by patients and the operators thereof (e.g., clinicians and other medical personnel). For example, some of these conventional balance systems employ displaceable background enclosures with fixed images imprinted thereon that are not readily adaptable to different testing schemes.

Therefore, what is needed is a force measurement system having a displaceable force measurement assembly that employs virtual reality scenarios for effectively assessing the balance characteristics of a subject and offering much greater flexibility in the balance assessment testing that can be employed. Moreover, what is needed is a force measurement system having a displaceable force measurement assembly which has a base assembly with a reduced step height so as to facilitate the use of the system by elderly individuals and those having balance disorders. Furthermore, a force measurement system having a displaceable force measurement assembly is needed that includes an immersive visual display device that enables a subject being tested to become effectively immersed in a virtual reality scenario or an interactive game.

BRIEF SUMMARY OF EMBODIMENTS OF THE INVENTION

Accordingly, the present invention is directed to a force measurement system having a displaceable force measurement assembly that substantially obviates one or more problems resulting from the limitations and deficiencies of the related art.

In accordance with one aspect of the present invention, there is provided a force measurement system having a displaceable force measurement assembly that includes: a force measurement assembly configured to receive a subject, the force measurement assembly including: a surface for receiving at least one portion of the body of the subject; and at least one force transducer, the at least one force transducer configured to sense one or more measured quantities and output one or more signals that are representative of forces and/or moments being applied to the surface of the force measurement assembly by the subject; at least one actuator operatively coupled to the force measurement assembly, the at least one actuator configured to displace the force measurement assembly; at least one visual display device having an output screen, the at least one visual display device configured to display one or more virtual reality scenes on the output screen so that the scenes are viewable by the subject, wherein the one or more virtual reality scenes are configured to create a simulated environment for the subject; and one or more data processing devices operatively coupled to the force measurement assembly, the at least one actuator, and the at least one visual display device, the one or more data processing devices configured to receive the one or more signals that are representative of the forces and/or moments being applied to the surface of the force measurement assembly by the subject, and to convert the one or more signals into output forces and/or moments, the one or more data processing devices further configured to selectively displace the force measurement assembly using the at least one actuator.

In a further embodiment of this aspect of the present invention, the at least one actuator is configured to rotate the force measurement assembly about at least one of: (i) a laterally extending rotational axis and (ii) a longitudinally extending rotational axis.

In yet a further embodiment, the at least one actuator is configured to rotate the force measurement assembly. In one more embodiments, the rotation of the force measurement assembly occurs about a laterally extending rotational axis.

In still a further embodiment, the at least one actuator is configured to translate the force measurement assembly in at least one of the following two directions: (i) a direction generally parallel to the sagittal plane of the subject and (ii) a direction generally parallel to the coronal plane of the subject.

In yet a further embodiment, the at least one actuator is configured to translate the force measurement assembly. In one more embodiments, the translation of the force measurement assembly occurs in a direction generally parallel to the sagittal plane of the subject.

In still a further embodiment, the one or more virtual reality scenes on the output screen of the at least one visual display device are in the form of one or more two-dimensional images or one or more three-dimensional images.

In yet a further embodiment, the one or more two-dimensional images or the one or more three-dimensional images comprise at least one of: (i) one or more images appearing to be displaced inwardly on the output screen of the at least one visual display device, (ii) one or more images appearing to be displaced outwardly on the output screen of the at least one visual display device, (iii) one or more images simulating the visual effects of walking down an aisle, and (iv) one or more images comprising an interactive game.

In still a further embodiment, the one or more data processing devices adjust the one or more virtual reality scenes on the output screen of the at least one visual display device in accordance with a computed sway angle for the subject.

In yet a further embodiment, the one or more data processing devices adjust the one or more virtual reality scenes on the output screen of the at least one visual display device in accordance with the selected displacement of the force measurement assembly.

In still a further embodiment, the force measurement system further comprises a motion detection system operatively coupled to the one or more data processing devices, the motion detection system configured to detect the motion of one or more body gestures of the subject, and the one or more data processing devices configured to adjust the one or more virtual reality scenes on the output screen of the at least one visual display device in accordance with the detected motion of the one or more body gestures of the subject.

In yet a further embodiment, the one or more body gestures of the subject comprise at least one of: (i) one or more limb movements of the subject, (ii) one or more torso movements of the subject, and (iii) a combination of one or more limb movements and one or more torso movements of the subject.

In accordance with another aspect of the present invention, there is provided a method for testing a subject disposed on a displaceable force measurement assembly, the method comprising the steps of: (i) providing a force measurement assembly configured to receive a subject, the force measurement assembly including: a surface for receiving at least one portion of the body of the subject; and at least one force transducer, the at least one force transducer configured to sense one or more measured quantities and output one or more signals that are representative of forces and/or moments being applied to the surface of the force measurement assembly by the subject; (ii) providing at least one actuator operatively coupled to the force measurement assembly, the at least one actuator configured to displace the force measurement assembly; (iii) providing at least one visual display device having an output screen, the at least one visual display device configured to display one or more virtual reality scenes on the output screen so that the scenes viewable by the subject; (iv) providing one or more data processing devices operatively coupled to the force measurement assembly, the at least one actuator, and the at least one visual display device, the one or more data processing devices configured to receive the one or more signals that are representative of the forces and/or moments being applied to the surface of the force measurement assembly by the subject and to convert the one or more signals into output forces and/or moments, and the one or more data processing devices configured to selectively displace the force measurement assembly using the at least one actuator; (v) positioning the subject on the force measurement assembly; (vi) selectively displacing the force measurement assembly and the subject disposed thereon using the at least one actuator; (vii) sensing, by utilizing the at least one force transducer, one or more measured quantities that are representative of forces and/or moments being applied to the surface of the force measurement assembly by the subject and outputting one or more signals representative thereof; (viii) converting, by using the one or more data processing devices, the one or more signals that are representative of the forces and/or moments being applied to the surface of the force measurement assembly by the subject into output forces and/or moments; and (ix) displaying one or more virtual reality scenes to the subject utilizing the output screen of the at least one visual display device, the one or more virtual reality scenes creating a simulated environment for the subject.

In a further embodiment of this aspect of the present invention, the method further comprises the steps of: (i) positioning the subject in a substantially stationary position on the force measurement assembly; and (ii) generating, by using the one or more data processing devices, one or more virtual reality scenes in the form of one or more two-dimensional images or one or more three-dimensional images that appear to be displaced inwardly on the output screen of the at least one visual display device so as to inhibit a sensory ability of the subject.

In yet a further embodiment, the method further comprises the steps of: (i) displacing the force measurement assembly and the subject disposed thereon using the at least one actuator so as to inhibit a sensory ability of the subject; and (ii) generating, by using the one or more data processing devices, one or more virtual reality scenes in the form of one or more substantially stationary two-dimensional images or three-dimensional images on the output screen of the at least one visual display device.

In still a further embodiment, the method further comprises the steps of: (i) displacing the force measurement assembly and the subject disposed thereon using the at least one actuator; and (ii) generating, by using the one or more data processing devices, one or more virtual reality scenes in the form of one or more two-dimensional images or one or more three-dimensional images that appear to be displaced inwardly on the output screen of the at least one visual display device so as to inhibit a sensory ability of the subject.

In accordance with yet another aspect of the present invention, there is provided a force measurement system having a displaceable force measurement assembly that includes: a force measurement assembly configured to receive a subject, the force measurement assembly including: a surface for receiving at least one portion of the body of the subject; and at least one force transducer, the at least one force transducer configured to sense one or more measured quantities and output one or more signals that are representative of forces and/or moments being applied to the surface of the force measurement assembly by the subject; at least one actuator operatively coupled to the force measurement assembly, the at least one actuator configured to displace the force measurement assembly; at least one visual display device having an output screen, the output screen of the at least one visual display device configured to at least partially surround the subject disposed on the force measurement assembly, the at least one visual display device configured to display one or more virtual reality scenes on the output screen so that the scenes are viewable by the subject, wherein the one or more virtual reality scenes are configured to create a simulated environment for the subject; and one or more data processing devices operatively coupled to the force measurement assembly, the at least one actuator, and the at least one visual display device, the one or more data processing devices configured to receive the one or more signals that are representative of the forces and/or moments being applied to the surface of the force measurement assembly by the subject, and the one or more data processing devices configured to selectively displace the force measurement assembly using the at least one actuator.

In a further embodiment of this aspect of the present invention, the output screen of the at least one visual display device engages enough of the peripheral vision of a subject such that the subject becomes immersed in the simulated environment.

In yet a further embodiment, the output screen of the at least one visual display at least partially circumscribes three sides of a subject.

In still a further embodiment, the force measurement system further comprises a base assembly in or on which the force measurement assembly and the at least one actuator are disposed, the base assembly having a width and a length, wherein a width of the output screen of the at least one visual display device is less than approximately 1.5 times the width of the base assembly, and wherein a depth of the output screen of the at least one visual display device is less than the length of the base assembly.

In yet a further embodiment, the width of the base assembly is measured in a direction generally parallel to the coronal plane of the subject, and wherein the length of the base assembly is measured in a direction generally parallel to the sagittal plane of the subject.

In still a further embodiment, the force measurement system further comprises a base assembly in or on which the force measurement assembly and the at least one actuator are disposed, wherein a width of the output screen of the at least one visual display device is not substantially greater than a width of the base assembly.

In yet a further embodiment, the at least one visual display comprises a projector, a convexly shaped mirror, and a concavely shaped projection screen, wherein the projector is configured to project an image onto the convexly shaped mirror, and the convexly shaped mirror is configured to project the image onto the concavely shaped projection screen.

In still a further embodiment, the concavely shaped projection screen is generally hemispherical in shape, and wherein the convexly shaped mirror is disposed near a top of the concavely shaped projection screen.

In yet a further embodiment, the top of the concavely shaped projection screen comprises a cutout for accommodating a light beam of the projector.

In still a further embodiment, the one or more data processing devices include a programmable logic controller configured to provide real-time control of the at least one actuator via an actuator control drive.

In yet a further embodiment, the programmable logic controller is configured to: (i) convert the one or more signals that are representative of the forces and/or moments being applied to the surface of the force measurement assembly by the subject into output forces and/or moments, (ii) compute center of pressure coordinates for the applied forces and/or compute a center of gravity value for the subject using the output forces and/or moments, and (iii) transmit the computed center of pressure coordinates and/or the computed center of gravity value to a computing device operatively coupled to the programmable logic controller.

In accordance with still another aspect of the present invention, there is provided a force measurement system having a displaceable force measurement assembly that includes: a force measurement assembly configured to receive a subject, the force measurement assembly including: a surface for receiving at least one portion of the body of the subject; and at least one force transducer, the at least one force transducer configured to sense one or more measured quantities and output one or more signals that are representative of forces and/or moments being applied to the surface of the force measurement assembly by the subject; at least one first actuator operatively coupled to the force measurement assembly, the at least one first actuator configured to rotate the force measurement assembly, the at least one first actuator disposed above the surface of the force measurement assembly; at least one second actuator operatively coupled to the force measurement assembly, the at least one second actuator configured to translate the force measurement assembly, the at least one second actuator disposed below the surface of the force measurement assembly; and one or more data processing devices operatively coupled to the force measurement assembly, the at least one first actuator, and the at least one second actuator, the one or more data processing devices configured to receive the one or more signals that are representative of the forces and/or moments being applied to the surface of the force measurement assembly by the subject and to convert the one or more signals into output forces and/or moments, the one or more data processing devices configured to selectively displace the force measurement assembly using the at least one first actuator and the at least one second actuator.

In a further embodiment of this aspect of the present invention, the force measurement system further comprises a base assembly in or on which the force measurement assembly and the first and second actuators are disposed, the base assembly having a step height measured from a ground surface to an upper surface thereof, wherein the step height of the base assembly is reduced, as compared to conventional dynamic force measurement systems, at least in part by the predetermined placement of the first and second actuators.

In yet a further embodiment, the step height of the base assembly is substantially less than conventional dynamic force measurement systems.

In still a further embodiment, the force measurement system further comprises a base assembly in or on which the force measurement assembly and the first and second actuators are disposed, the base assembly having a step height measured from a ground surface to an upper surface thereof, wherein a placement of the at least one first actuator above the surface of the force measurement assembly results in a reduction of the step height of the base assembly.

In yet a further embodiment, the one or more data processing devices include a programmable logic controller configured to provide real-time control of the at least one first actuator and the at least one second actuator via an actuator control drive.

In accordance with yet another aspect of the present invention, there is provided a force measurement system having a displaceable force measurement assembly that includes: a force measurement assembly configured to receive a subject, the force measurement assembly including: a surface for receiving at least one portion of the body of the subject; and at least one force transducer, the at least one force transducer configured to sense one or more measured quantities and output one or more signals that are representative of forces and/or moments being applied to the surface of the force measurement assembly by the subject; at least one actuator operatively coupled to the force measurement assembly, the at least one actuator configured to displace the force measurement assembly; at least one visual display device having an output screen, the at least one visual display device configured to display an interactive game on the output screen so that the interactive game is viewable by the subject; and a data processing device operatively coupled to the force measurement assembly, the at least one actuator, and the at least one visual display device, the data processing device configured to receive the one or more signals that are representative of forces and/or moments being applied to the surface of the force measurement assembly and to compute one or more numerical values using the one or more signals, the data processing device being configured to control the movement of at least one manipulatable element of the interactive game displayed on the output screen of the at least one visual display device by using the one or more computed numerical values.

In a further embodiment of this aspect of the present invention, the data processing device is further configured to quantify a subject's performance while playing the interactive game using one or more performance parameters, and to assess the balance of the subject by utilizing the one or more performance parameters.

In yet a further embodiment, a difficulty or skill level of the interactive game progressively increases over time.

In still a further embodiment, the force measurement system further comprises a motion detection system operatively coupled to the data processing device, the motion detection system configured to detect the motion of one or more body gestures of the subject, and the data processing device configured to adjust the interactive game on the output screen of the at least one visual display device in accordance with the detected motion of the one or more body gestures of the subject.

In yet a further embodiment, the one or more body gestures of the subject comprise at least one of: (i) one or more limb movements of the subject, (ii) one or more torso movements of the subject, and (iii) a combination of one or more limb movements and one or more torso movements of the subject.

In accordance with still another aspect of the present invention, there is provided a force measurement system that includes: a force measurement assembly configured to receive a subject, the force measurement assembly including: a surface for receiving at least one portion of the body of the subject; and at least one force transducer, the at least one force transducer configured to sense one or more measured quantities and output one or more signals that are representative of forces and/or moments being applied to the surface of the force measurement assembly by the subject; a motion detection system, the motion detection system configured to detect the motion of one or more body gestures of the subject; at least one visual display device having an output screen, the at least one visual display device configured to display one or more virtual reality scenes on the output screen so that the scenes are viewable by the subject, wherein the one or more virtual reality scenes are configured to create a simulated environment for the subject; and a data processing device operatively coupled to the force measurement assembly, the motion detection system, and the at least one visual display device, the data processing device configured to receive the one or more signals that are representative of the forces and/or moments being applied to the surface of the force measurement assembly by the subject, and the data processing device configured to adjust the one or more virtual reality scenes on the output screen of the at least one visual display device in accordance with at least one of: (i) the forces and/or moments being applied to the surface of the force measurement assembly by the subject and (ii) the detected motion of the one or more body gestures of the subject.

In a further embodiment of this aspect of the present invention, the one or more body gestures of the subject comprise at least one of: (i) one or more limb movements of the subject, (ii) one or more torso movements of the subject, and (iii) a combination of one or more limb movements and one or more torso movements of the subject.

In yet a further embodiment, the output screen of the at least one visual display device engages enough of the peripheral vision of a subject such that the subject becomes immersed in the simulated environment.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
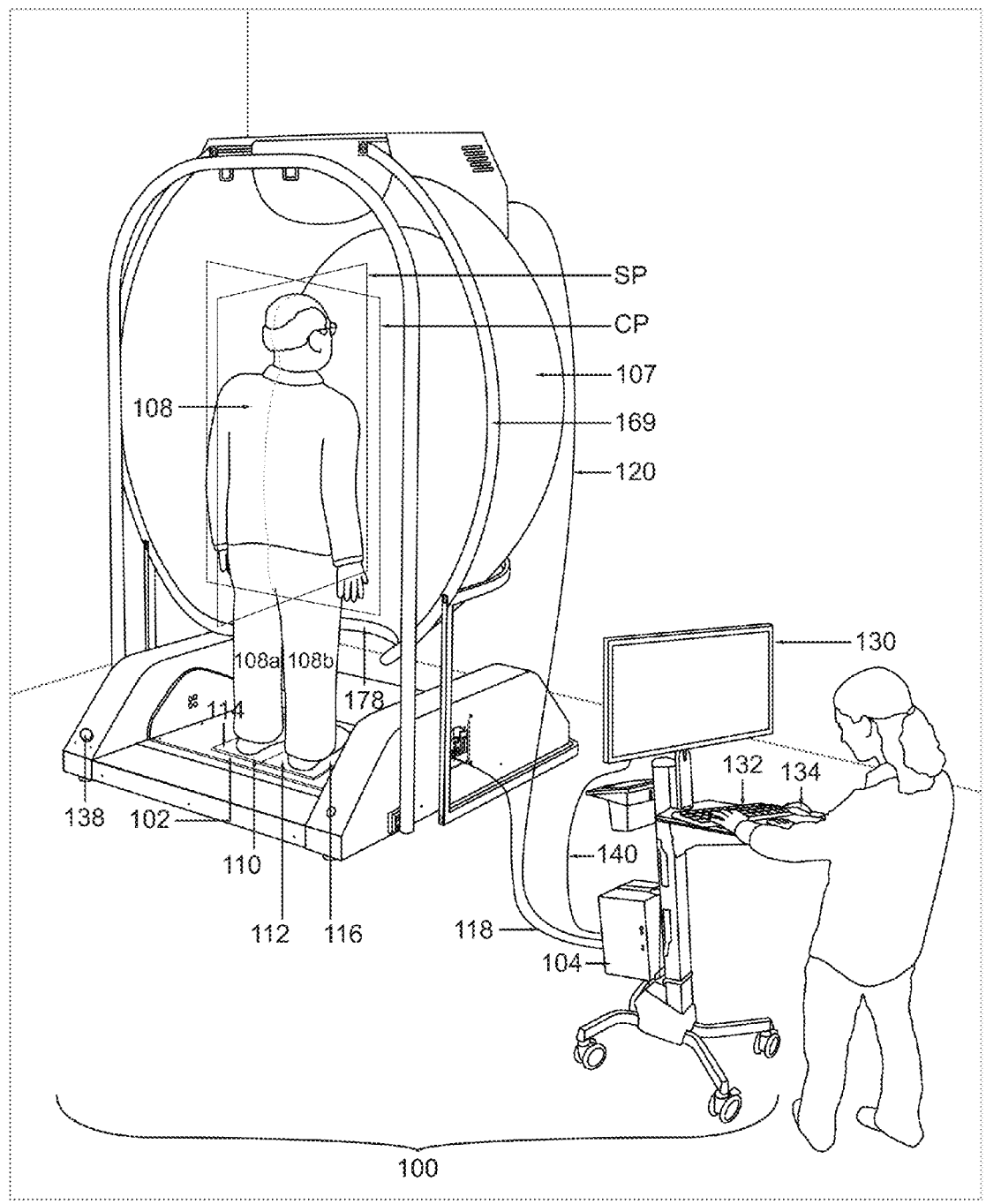
FIG. 1 is a diagrammatic perspective view of a force measurement system having a displaceable force measurement assembly according to an embodiment of the invention.

An exemplary embodiment of the measurement and testing system is seen generally at 100 in FIG. 1. In the illustrative embodiment, the force measurement system 100 generally comprises a force measurement assembly 102 that is operatively coupled to a data acquisition/data processing device 104 (i.e., a data acquisition and processing device or computing device that is capable of collecting, storing, and processing data), which in turn, is operatively coupled to a subject visual display device 107 and an operator visual display device 130. As illustrated in FIG. 1, the force measurement assembly 102 is configured to receive a subject 108 thereon, and is capable of measuring the forces and/or moments applied to its measurement surfaces 114, 116 by the subject 108.

As shown in FIG. 1, the data acquisition/data processing device 104 includes a plurality of user input devices 132, 134 connected thereto. Preferably, the user input devices 132, 134 comprise a keyboard 132 and a mouse 134. In addition, the operator visual display device 130 may also serve as a user input device if it is provided with touch screen capabilities. While a desktop-type computing system is depicted in FIG. 1, one of ordinary skill in the art will appreciate that another type of data acquisition/data processing device 104 can be substituted for the desktop computing system such as, but not limited to, a laptop or a palmtop computing device (i.e., a PDA). In addition, rather than providing a data acquisition/data processing device 104, it is to be understood that only a data acquisition device could be provided without departing from the spirit and the scope of the invention.

Referring again to FIG. 1, it can be seen that the force measurement assembly 102 of the illustrated embodiment is in the form of a displaceable, dual force plate assembly. The displaceable, dual force plate assembly includes a first plate component 110, a second plate component 112, at least one force measurement device (e.g., a force transducer) associated with the first plate component 110, and at least one force measurement device (e.g., a force transducer) associated with the second plate component 112. In the illustrated embodiment, a subject 108 stands in an upright position on the force measurement assembly 102 and each foot of the subject 108 is placed on the top surfaces 114, 116 of a respective plate component 110, 112 (i.e., one foot on the top surface 114 of the first plate component 110 and the other foot on the top surface 116 of the second plate component 112). The at least one force transducer associated with the first plate component 110 is configured to sense one or more measured quantities and output one or more first signals that are representative of forces and/or moments being applied to its measurement surface 114 by the left foot/leg 108a of the subject 108, whereas the at least one force transducer associated with the second plate component 112 is configured to sense one or more measured quantities and output one or more second signals that are representative of forces and/or moments being applied to its measurement surface 116 by the right foot/leg 108b of subject 108.

In one non-limiting, exemplary embodiment, the force plate assembly 102 has a load capacity of up to approximately 500 lbs. (up to approximately 2,224 N) or up to 500 lbs. (up to 2,224 N). Advantageously, this high load capacity enables the force plate assembly 102 to be used with almost any subject requiring testing on the force plate assembly 102. Also, in one non-limiting, exemplary embodiment, the force plate assembly 102 has a footprint of approximately eighteen (18) inches by twenty (20) inches. However, one of ordinary skill in the art will realize that other suitable dimensions for the force plate assembly 102 may also be used.

Figure 2:
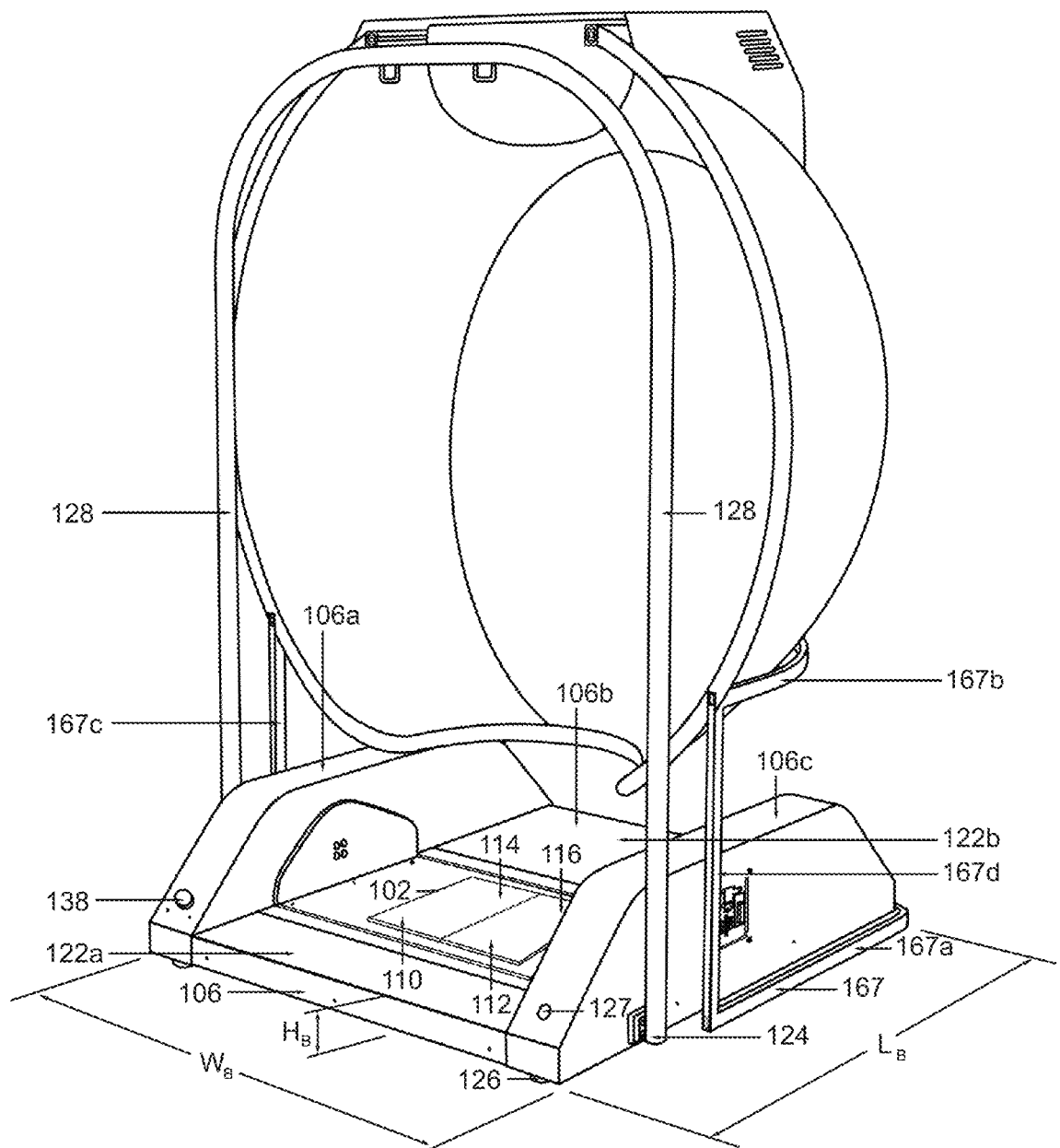
FIG. 2 is a perspective view of an immersive subject visual display device, a base assembly, and displaceable force measurement assembly of the force measurement system according to an embodiment of the invention.

Now, with reference to FIG. 2, it can be seen that the displaceable force measurement assembly 102 is movably coupled to a base assembly 106. The base assembly 106 generally comprises a substantially planar center portion 106b with two spaced-apart side enclosures 106a, 106c that are disposed on opposed sides of the center portion 106b. As shown in FIG. 2, the displaceable force measurement assembly 102 is recessed-mounted into the top surface of the center portion 106b of the base assembly 106 so that its upper surface lies substantially flush with the adjacent stationary top surfaces 122a, 122b of the center portion 106b of the base assembly 106. Also, in the illustrated embodiment, it can be seen that the base assembly 106 further includes a pair of mounting brackets 124 disposed on the outward-facing side surfaces of each side enclosure 106a, 106c. Each mounting bracket 124 accommodates a respective support rail 128. The support rails 128 can be used for various purposes related to the force measurement system 100. For example, the support rails 128 can be used for supporting a safety harness system, which is worn by the subject during testing so as to prevent injury.

Referring again to FIG. 2, each side enclosure 106a, 106c houses a plurality of electronic components that generate a significant amount of waste heat that requires venting. Because the bottom of each side enclosure 106a, 106c is substantially open, the waste heat is vented through the bottom thereof. In FIG. 2, it can be seen that the side enclosure 106a comprises an emergency stop switch 138 (E-stop) provided in the rear, diagonal panel thereof. In one embodiment, the emergency stop switch 138 is in the form of a red pushbutton that can be easily pressed by a user of the force measurement system 100 in order to quasi-instantaneously stop the displacement of the force measurement assembly 102. As such, the emergency stop switch 138 is a safety mechanism that protects a subject disposed on the displaceable force measurement assembly 102 from potential injury.

Figure 3:
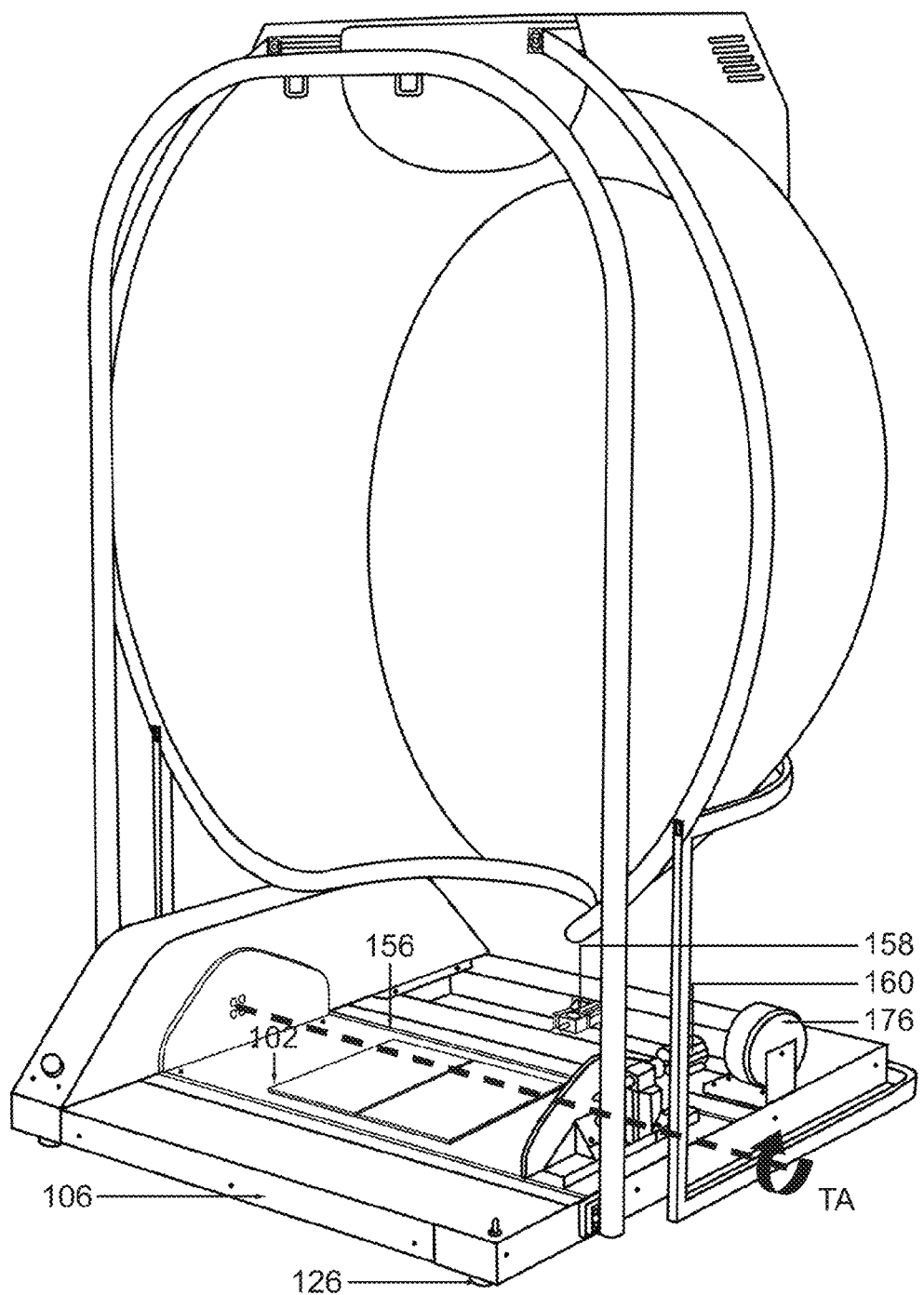
FIG. 3 is a perspective view of an immersive subject visual display device and a cutaway perspective view of a base assembly and displaceable force measurement assembly of the force measurement system according to an embodiment of the invention, wherein several covers of the base assembly are removed.

Next, turning to FIG. 3, the drive components of the base assembly 106 will be described in detail. Initially, the actuator system for producing the translation of the force measurement assembly 102 will be explained. In FIG. 3, the front top cover of the center portion 106b of the base assembly 106 has been removed to reveal the translation drive components. As shown in this figure, the force measurement assembly 102 is rotatably mounted to a translatable sled assembly 156. The translatable sled assembly 156 is displaced forward and backward (i.e., in directions generally parallel to the sagittal plane SP of the subject (see e.g., FIG. 1) disposed on the force measurement assembly 102) by means of a first actuator assembly 158. In the illustrated embodiment, the first actuator assembly 158 is in the form of ball screw actuator, and includes an electric motor that drives a rotatable screw shaft which, in turn, is threadingly coupled to a nut fixedly secured to the translatable sled assembly 156. As such, when the screw shaft of the first actuator assembly 158 is rotated by the electric motor, the translatable sled assembly is displaced forward and backward along a substantially linear path. The electric motor of the first actuator assembly 158 is operatively coupled to a gear box (e.g., a 4:1 gear box) which, in turn, drives the rotatable screw shaft. Advantageously, because the nut of the ball screw actuator runs on ball bearings, friction is minimized and the actuator assembly 158 is highly efficient. However, an undesirable consequence of the highly efficient ball screw actuator design is its back-driveability. This poses a potential safety hazard to a subject disposed on the displaceable force measurement assembly 102 because the force plate could inadvertently move when a subject's weight is applied thereto. In order to prevent the force measurement assembly 102 from inadvertently being translated, the first actuator assembly 158 is additionally provided with a brake assembly disposed adjacent to the electric motor thereof. The brake assembly of the first actuator assembly 158 prevents any unintentional translation of the force measurement assembly 102.

Again, referring to FIG. 3, the actuator system for producing the rotation of the force measurement assembly 102 will now be described. In FIG. 3, the top cover of the side enclosure 106c of the base assembly 106 has been removed to reveal the rotational drive components. The force measurement assembly 102 is rotated within the translatable sled assembly 156 by a second actuator assembly 160. Like the first actuator assembly 158, the second actuator assembly 160 is also in the form of ball screw actuator, and includes an electric motor with a gear box (e.g., a 4:1 gear box) that drives a rotatable screw shaft which, in turn, is threadingly coupled to a nut that runs on ball bearings. Although, unlike the first actuator assembly 158, the second actuator assembly 160 further includes a swing arm which is operatively coupled to the nut of the ball screw actuator. When the nut undergoes displacement along the screw shaft, the swing arm, which is attached to the force measurement assembly 102, is rotated. As such, when the swing arm is rotated, the force measurement assembly 102 is also rotated about a transverse rotational axis TA (see FIG. 3). In one embodiment, the imaginary transverse rotational axis TA approximately passes through the center of the ankle joints of subject when he or she is disposed on the force measurement assembly 102. Because the second actuator assembly 160 is also in the form of a highly efficient ball screw actuator, it includes a brake assembly disposed adjacent to the electric motor to prevent it from being back-driven, similar to that of the first actuator assembly 158. The brake assembly of the second actuator assembly 160 prevents the force measurement assembly 102 from being inadvertently rotated so as to protect a subject disposed thereon from its inadvertent movement. When the translatable sled assembly 156 is translated by the first actuator assembly 158, the second actuator assembly 160 is translated with the sled assembly 156 and the force plate.

In a preferred embodiment of the invention, both the first actuator assembly 158 and the second actuator assembly 160 are provided with two (2) electrical cables operatively coupled thereto. The first cable connected to each actuator assembly 158, 160 is a power cable for the electric motor and brake of each actuator, while the second cable transmits positional information from the respective actuator encoder that is utilized in the feedback control of each actuator assembly 158, 160.

Referring back to FIG. 1, it can be seen that the base assembly 106 is operatively coupled to the data acquisition/data processing device 104 by virtue of an electrical cable 118. The electrical cable 118 is used for transmitting data between the programmable logic controller (PLC) of the base assembly 106 and the data acquisition/data processing device 104 (i.e., the operator computing device 104). Various types of data transmission cables can be used for cable 118. For example, the cable 118 can be a Universal Serial Bus (USB) cable or an Ethernet cable. Preferably, the electrical cable 118 contains a plurality of electrical wires bundled together that are utilized for transmitting data. However, it is to be understood that the base assembly 106 can be operatively coupled to the data acquisition/data processing device 104 using other signal transmission means, such as a wireless data transmission system.

Figure 4:
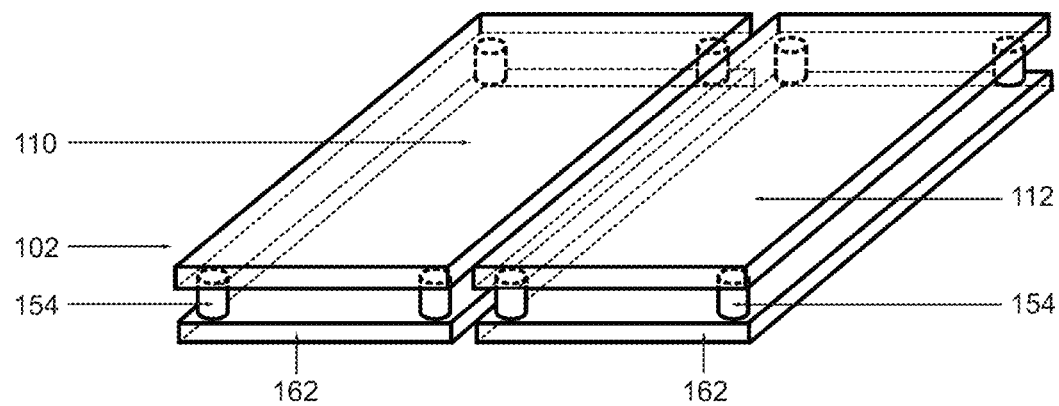
FIG. 4 is a diagrammatic perspective view of one measurement assembly used in the force measurement system, according to an embodiment of the invention, wherein the measurement assembly is in the form of a dual force plate.

In the illustrated embodiment, the at least one force transducer associated with the first and second plate components 110, 112 comprises four (4) pylon-type force transducers 154 (or pylon-type load cells) that are disposed underneath, and near each of the four corners (4) of the first plate component 110 and the second plate component 112 (see FIG. 4). Each of the eight (8) illustrated pylon-type force transducers has a plurality of strain gages adhered to the outer periphery of a cylindrically-shaped force transducer sensing element for detecting the mechanical strain of the force transducer sensing element imparted thereon by the force(s) applied to the surfaces of the force measurement assembly 102. As shown in FIG. 4, a respective base plate 162 can be provided underneath the transducers 154 of each plate component 110, 112 for facilitating the mounting of the force plate assembly to the translatable sled assembly 156 of the base assembly 106. Alternatively, a plurality of structural frame members (e.g., formed from steel) could be used in lieu of the base plates 162 for attaching the dual force plate assembly to the translatable sled assembly 156 of the base assembly 106.

In an alternative embodiment, rather than using four (4) pylon-type force transducers 154 on each plate component 110, 112, force transducers in the form of transducer beams could be provided under each plate component 110, 112. In this alternative embodiment, the first plate component 110 could comprise two transducer beams that are disposed underneath, and on generally opposite sides of the first plate component 110. Similarly, in this embodiment, the second plate component 112 could comprise two transducer beams that are disposed underneath, and on generally opposite sides of the second plate component 112. Similar to the pylon-type force transducers 154, the force transducer beams could have a plurality of strain gages attached to one or more surfaces thereof for sensing the mechanical strain imparted on the beam by the force(s) applied to the surfaces of the force measurement assembly 102.

Rather, than using four (4) force transducer pylons under each plate, or two spaced apart force transducer beams under each plate, it is to be understood that the force measurement assembly 102 can also utilize the force transducer technology described in pending patent application Ser. No. 13/348,506, the entire disclosure of which is incorporated herein by reference.

Figure 6:
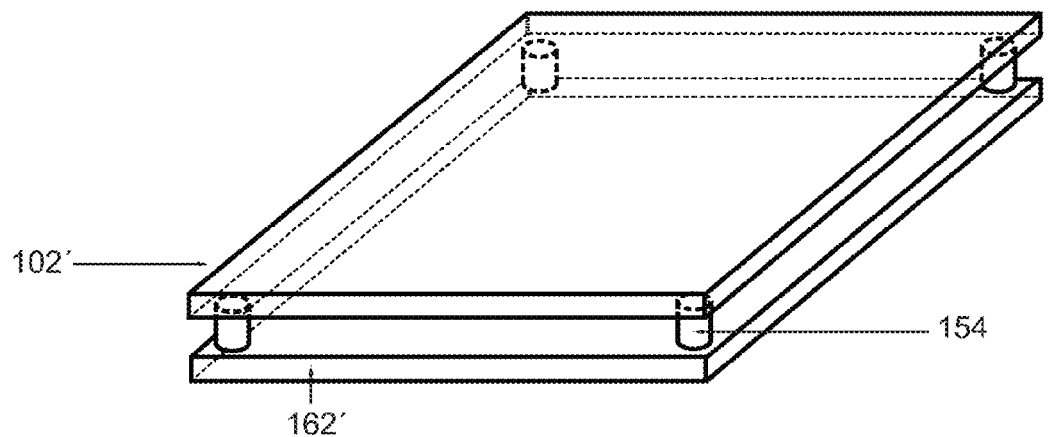
FIG. 6 is a diagrammatic perspective view of another measurement assembly used in the force measurement system, according to an embodiment of the invention, wherein the measurement assembly is in the form of a single force plate.

In other embodiments of the invention, rather than using a force measurement assembly 102 having first and second plate components 110, 112, it is to be understood that a force measurement assembly 102' in the form of a single force plate may be employed (see FIG. 6). Unlike the dual force plate assembly illustrated in FIGS. 1 and 4, the single force plate comprises a single measurement surface on which both of a subject's feet are placed during testing. Although, similar to the measurement assembly 102, the illustrated single force plate 102' comprises four (4) pylon-type force transducers 154 (or pylon-type load cells) that are disposed underneath, and near each of the four corners (4) thereof for sensing the load applied to the surface of the force measurement assembly 102'. Also, referring to FIG. 6, it can be seen that the single force plate 102' may comprise a single base plate 162' disposed beneath the four (4) pylon-type force transducers 154.

Referring to FIGS. 2 and 3, the base assembly 106 is preferably provided with a plurality of support feet 126 disposed thereunder. Preferably, each of the four (4) corners of the base assembly 106 is provided with a support foot 126. In one embodiment, each support foot 126 is attached to a bottom surface of base assembly 106. In one preferred embodiment, at least one of the support feet 126 is adjustable so as to facilitate the leveling of the base assembly 106 on an uneven floor surface (e.g., see FIG. 3, the support foot can be provided with a threaded shaft that permits the height thereof to be adjusted). For example, referring to FIG. 2, the right corner of the base assembly 106 may be provided with a removable cover plate 127 for gaining access to an adjustable support foot 126.

In one exemplary embodiment, with reference to FIG. 2, the base assembly 106 has a length $L_B$ of approximately five feet (5'-0"), a width $W_B$ of approximately five feet (5'-0"), and a step height $H_B$ of approximately four (4) inches. In other words, the base assembly has an approximately 5'-0" by 5'-0" footprint with step height of approximately four (4) inches. In other exemplary embodiments, the base assembly 106 has a width $W_B$ of slightly less than five feet (5'-0"), for example, a width $W_B$ lying in the range between approximately fifty-two (52) inches and approximately fifty-nine (59) inches (or between fifty-two (52) inches and fifty-nine (59) inches). Also, in other exemplary embodiments, the base assembly 106 has a step height lying in the range between approximately four (4) inches and approximately four and one-half (4½) inches (or between four (4) inches and four and one-half (4½) inches). Advantageously, the design of the base assembly 106 is such that its step height is minimized. For example, the placement of the second actuator assembly 160 above the top surface of the base assembly 106 facilitates a reduction in the step height of the base assembly 106. It is highly desirable for the base assembly 106 to have as low a profile as possible. A reduced step height especially makes it easier for subjects having balance disorders to step on and off the base assembly 106. This reduced step height is particularly advantageous for elderly subjects or patients being tested on the force measurement system 100 because it is typically more difficult for elderly subjects to step up and down from elevated surfaces.

Figure 8:
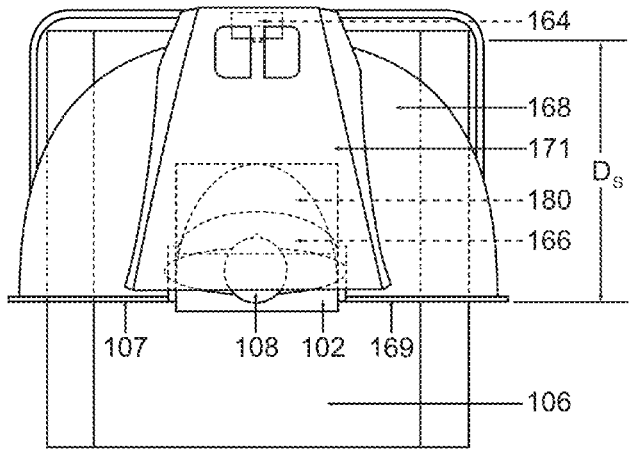
FIG. 8 is a diagrammatic top view of the base assembly and the immersive subject visual display device of the force measurement system according to an embodiment of the invention.
Figure 9:
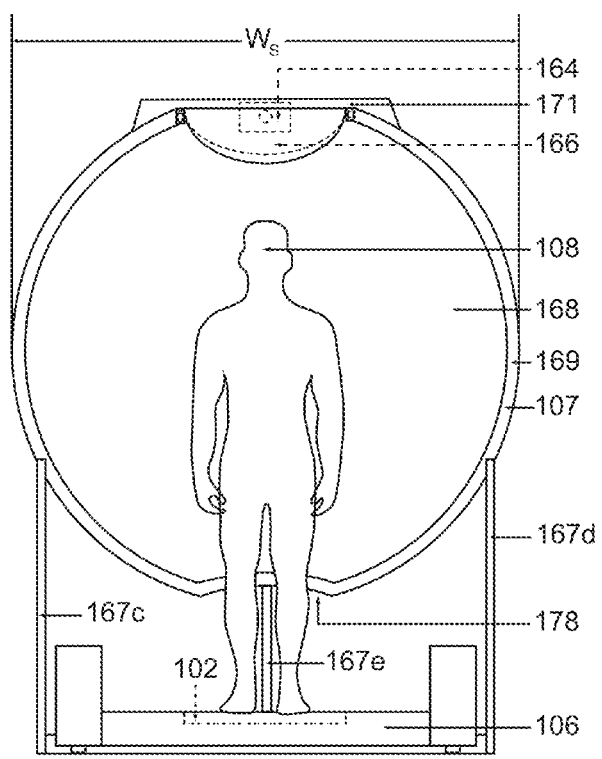
FIG. 9 is a diagrammatic rear view of the base assembly and the immersive subject visual display device of the force measurement system according to an embodiment of the invention.
Figure 10:
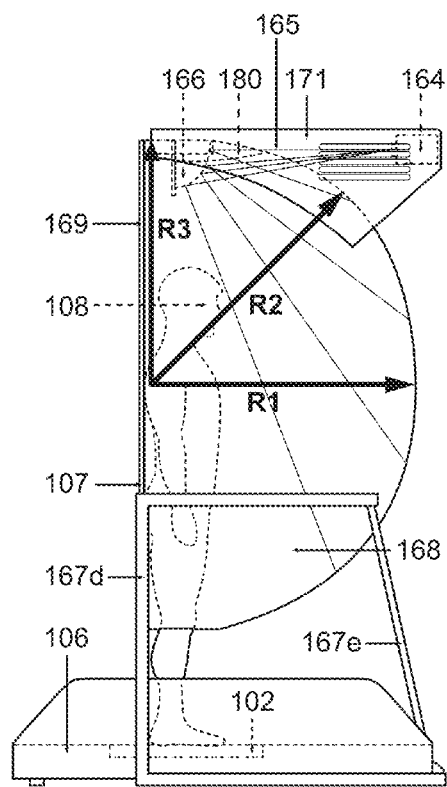
FIG. 10 is a diagrammatic side view of the base assembly and the immersive subject visual display device of the force measurement system according to an embodiment of the invention.

Now, with reference to FIGS. 8-10, the subject visual display device 107 of the force measurement system 100 will be described in more detail. In the illustrated embodiment, the subject visual display device 107 generally comprises a projector 164, a generally spherical mirror 166 (i.e., a convexly curved mirror that has the shape of a piece cut out of a spherical surface), and a generally hemispherical concave projection screen 168 with a variable radius (i.e., the radius of the hemispherical projection screen 168 becomes increasingly larger from its center to its periphery—see radii R1, R2, and R3 in FIG. 10). As shown in FIGS. 8-10, the hemispherical projection screen 168 may be provided with a peripheral flange 169 therearound. The lens of the projector 164 projects an image onto the generally spherical mirror 166 which, in turn, projects the image onto the generally hemispherical projection screen 168 (see FIG. 10). As shown in FIGS. 8 and 10, the top of the generally hemispherical projection screen 168 is provided with a semi-circular cutout 180 for accommodating the projector light beam 165 in the illustrative embodiment. Advantageously, the generally hemispherical projection screen 168 is a continuous curved surface that does not contain any lines or points resulting from the intersection of adjoining planar or curved surfaces. Thus, the projection screen 168 is capable of creating a completely immersive visual environment for a subject being tested on the force measurement assembly 102 because the subject is unable to focus on any particular reference point or line on the screen 168. As such, the subject becomes completely immersed in the virtual reality scene(s) being projected on the generally hemispherical projection screen 168, and thus, his or her visual perception can be effectively altered during a test being performed using the force measurement system 100 (e.g., a balance test). In order to permit a subject to be substantially circumscribed by the generally hemispherical projection screen 168 on three sides, the bottom of the screen 168 is provided with a semi-circular cutout 178 in the illustrative embodiment.

In one embodiment of the invention, the generally hemispherical projection screen 168 is formed from a suitable material (e.g., an acrylic, fiberglass, fabric, aluminum, etc.) having a matte gray color. A matte gray color is preferable to a white color because it minimizes the unwanted reflections that can result from the use of a projection screen having a concave shape. Also, in an exemplary embodiment, the projection screen 168 has a diameter (i.e., width $W_S$) of approximately 69 inches and a depth $D_S$ of approximately 22 inches. In other exemplary embodiments, the projection screen 168 has a width $W_S$ lying in the range between approximately sixty-eight (68) inches and approximately seventy-four (74) inches (or between sixty-eight (68) inches and seventy-four (74) inches). For example, including the flange 169, the projection screen 168 could have a width $W_S$ of approximately seventy-three (73) inches. In some embodiments, the target distance between the subject and the front surface of the projection screen 168 can lie within the range between approximately 25 inches and approximately 40 inches (or between 25 inches and 40 inches). Although, those of ordinary skill in the art will readily appreciate that other suitable dimensions and circumscribing geometries may be utilized for the projection screen 168, provided that the selected dimensions and circumscribing geometries for the screen 168 are capable of creating an immersive environment for a subject disposed on the force measurement assembly 102 (i.e., the screen 168 of the subject visual display device engages enough of the subject's peripheral vision such that the subject becomes, and remains immersed in the virtual reality scenario). In one or more embodiments, the projection screen 168 fully encompasses the peripheral vision of the subject 108 (e.g., by the coronal plane CP of the subject being approximately aligned with the flange 169 of the projection screen 168 or by the coronal plane CP being disposed inwardly from the flange 169 within the hemispherical confines of the screen 168). In other words, the output screen 168 of the at least one visual display 107 at least partially circumscribes three sides of a subject 108 (e.g., see FIG. 1). Moreover, those of ordinary skill in the art will also appreciate that the subject visual display device 107 may utilize other suitable projection means. For example, rather using an overhead-type projector 164 as illustrated in FIGS. 8-10, a direct or rear projection system can be utilized for projecting the image onto the screen 168, provided that the direct projection system does not interfere with the subject's visibility of the target image. In such a rear or direct projection arrangement, the generally spherical mirror 166 would not be required. In one exemplary alternative embodiment, a single projector with a fisheye-type lens and no mirror is utilized in the subject visual display system. As shown in FIGS. 8-10, a top cover 171 is preferably provided over the projector 164, the mirror 166, and the cutout 180 in the output screen 168 so as to protect these components, and to give the visual display device 107 a more finished appearance.

In one or more embodiments, the base assembly 106 has a width $W_B$ (see e.g., FIG. 2) measured in a direction generally parallel to the coronal plane CP of the subject (see e.g., FIG. 1) and a length $L_B$ (FIG. 2) measured in a direction generally parallel to the sagittal plane SP of the subject (FIG. 1). In these one or more embodiments, a width $W_S$ of the output screen 168 of the at least one visual display device 107 (see FIG. 9) is less than approximately 1.5 times the width $W_B$ of the base assembly 106 (or less than 1.5 times the width $W_B$ of the base assembly 106), and a depth $D_S$ of the output screen 168 of the at least one visual display device 107 (see FIG. 8) is less than the length $L_B$ of the base assembly 106 (FIG. 2).

As illustrated in FIGS. 2 and 8-10, the generally hemispherical projection screen 168 can be supported from a floor surface using a screen support structure 167. In other words, the screen support structure 167 is used to elevate the projection screen 168 a predetermined distance above the floor of a room. With continued reference to FIGS. 2 and 8-10, it can be seen that the illustrated screen support structure 167 comprises a lower generally U-shaped member 167a, an upper generally U-shaped member 167b, and a plurality of vertical members 167c, 167d, 167e. As best shown in FIGS. 2, 9, and 10, the two vertical members 167c, 167d are disposed on opposite sides of the screen 168, while the third vertical member 167e is disposed generally in the middle of, and generally behind, the screen 168.

Next, referring again to FIG. 1, the operator visual display device 130 of the force measurement system 100 will be described in more particularity. In the illustrated embodiment, the operator visual display device 130 is in the form of a flat panel monitor. Those of ordinary skill in the art will readily appreciate that various types of flat panel monitors having various types of data transmission cables 140 may be used to operatively couple the operator visual display device 130 to the data acquisition/data processing device 104. For example, the flat panel monitor employed may utilize a video graphics array (VGA) cable, a digital visual interface (DVI or DVI-D) cable, a high-definition multimedia interface (HDMI or Mini-HDMI) cable, or a DisplayPort digital display interface cable to connect to the data acquisition/data processing device 104. Alternatively, in other embodiments of the invention, the visual display device 130 can be operatively coupled to the data acquisition/data processing device 104 using wireless data transmission means. Electrical power is supplied to the visual display device 130 using a separate power cord that connects to a building wall receptacle.

Also, as shown in FIG. 1, the subject visual display device 107 is operatively coupled to the data acquisition/data processing device 104 by means of a data transmission cable 120. More particularly, the projector 164 of the subject visual display device 107 is operatively connected to the data acquisition/data processing device 104 via the data transmission cable 120. Like the data transmission cable 140 described above for the operator visual display device 130, various types of data transmission cables 120 can be used to operatively connect the subject visual display device 107 to the data acquisition/data processing device 104 (e.g., the various types described above).

Those of ordinary skill in the art will appreciate that the visual display device 130 can be embodied in various forms. For example, if the visual display device 130 is in the form of flat screen monitor as illustrated in FIG. 1, it may comprise a liquid crystal display (i.e., an LCD display), a light-emitting diode display (i.e., an LED display), a plasma display, a projection-type display, or a rear projection-type display. The operator visual display device 130 may also be in the form of a touch pad display. For example, the operator visual display device 130 may comprise multi-touch technology which recognizes two or more contact points simultaneously on the surface of the screen so as to enable users of the device to use two fingers for zooming in/out, rotation, and a two finger tap.

Figure 11:
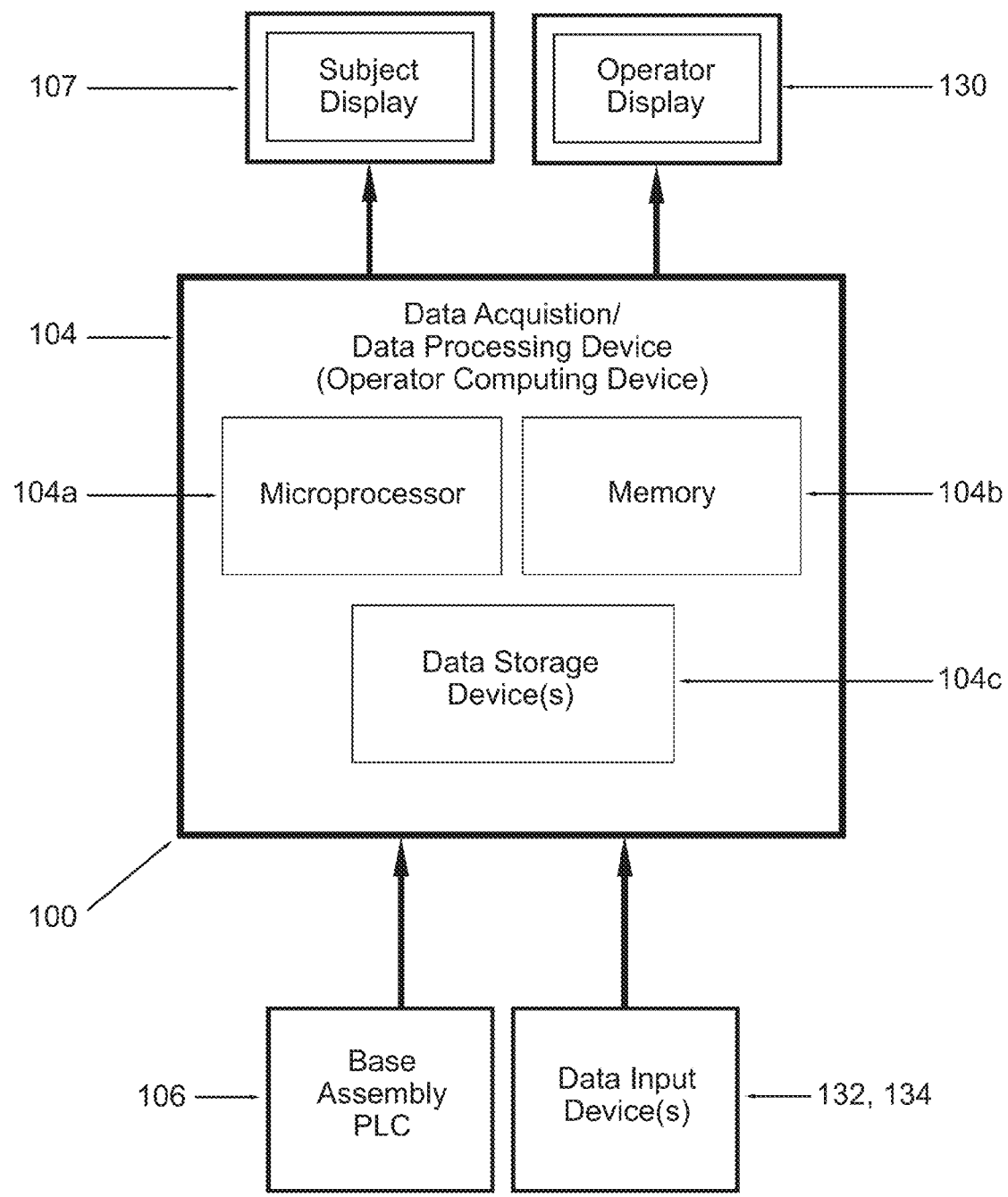
FIG. 11 is a block diagram of constituent components of the force measurement system having a displaceable force measurement assembly, according to an embodiment of the invention.

Now, turning to FIG. 11, it can be seen that the illustrated data acquisition/data processing device 104 (i.e., the operator computing device) of the force measurement system 100 includes a microprocessor 104a for processing data, memory 104b (e.g., random access memory or RAM) for storing data during the processing thereof, and data storage device(s) 104c, such as one or more hard drives, compact disk drives, floppy disk drives, flash drives, or any combination thereof. As shown in FIG. 11, the programmable logic controller (PLC) of the base assembly 106, the subject visual display device 107, and the operator visual display device 130 are operatively coupled to the data acquisition/data processing device 104 such that data is capable of being transferred between these devices 104, 106, 107, and 130. Also, as illustrated in FIG. 11, a plurality of data input devices 132, 134 such as the keyboard 132 and mouse 134 shown in FIG. 1, are operatively coupled to the data acquisition/data processing device 104 so that a user is able to enter data into the data acquisition/data processing device 104. In some embodiments, the data acquisition/data processing device 104 can be in the form of a desktop computer, while in other embodiments, the data acquisition/data processing device 104 can be embodied as a laptop computer.

Advantageously, the programmable logic controller 172 of the base assembly 106 (see e.g., FIGS. 12 and 13, which is a type of data processing device) provides real-time control of the actuator assemblies 158, 160 that displace the force measurement assembly 102 (i.e, force plate assembly 102). The real-time control provided by the programmable logic controller 172 ensures that the motion control software regulating the displacement of the force plate assembly 102 operates at the design clock rate, thereby providing fail-safe operation for subject safety. In one embodiment, the programmable logic controller 172 comprises both the motion control software and the input/output management software, which controls the functionality of the input/output (I/O) module of the programmable logic controller 172. In one embodiment, the programmable logic controller 172 utilizes EtherCAT protocol for enhanced speed capabilities and real-time control.

In one or more embodiments, the input/output (I/O) module of the programmable logic controller 172 allows various accessories to be added to the force measurement system 100. For example, an eye movement tracking system, such as that described by U.S. Pat. Nos. 6,113,237 and 6,152,564 could be operatively connected to the input/output (I/O) module of the programmable logic controller 172. As another example, a head movement tracking system, which is instrumented with one or more accelerometers, could be operatively connected to the input/output (I/O) module.

Figure 12:
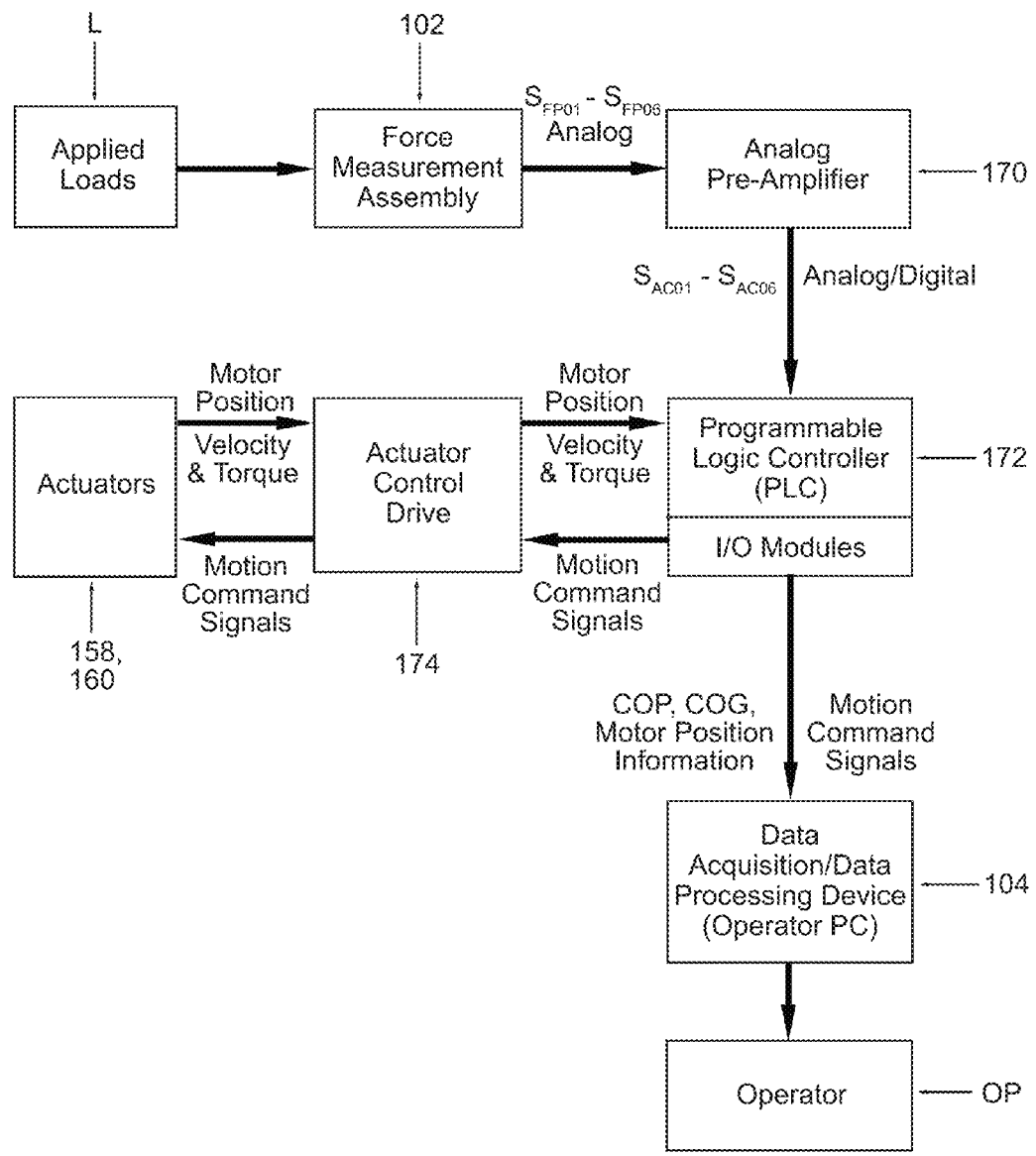
FIG. 12 is a block diagram illustrating data manipulation operations and motion control operations carried out by the force measurement system, according to an embodiment of the invention.

FIG. 12 graphically illustrates the acquisition and processing of the load data and the control of the actuator assemblies 158, 160 carried out by the exemplary force measurement system 100. Initially, as shown in FIG. 12, a load L is applied to the force measurement assembly 102 by a subject disposed thereon. The load is transmitted from the first and second plate components 110, 112 to its respective set of pylon-type force transducers or force transducer beams. As described above, in one embodiment of the invention, each plate component 110, 112 comprises four (4) pylon-type force transducers 154 disposed thereunder. Preferably, these pylon-type force transducers 154 are disposed near respective corners of each plate component 110, 112. In a preferred embodiment of the invention, each of the pylon-type force transducers includes a plurality of strain gages wired in one or more Wheatstone bridge configurations, wherein the electrical resistance of each strain gage is altered when the associated portion of the associated pylon-type force transducer undergoes deformation resulting from the load (i.e., forces and/or moments) acting on the first and second plate components 110, 112. For each plurality of strain gages disposed on the pylon-type force transducers, the change in the electrical resistance of the strain gages brings about a consequential change in the output voltage of the Wheatstone bridge (i.e., a quantity representative of the load being applied to the measurement surface). Thus, in one embodiment, the four (4) pylon-type force transducers 154 disposed under each plate component 110, 112 output a total of three (3) analog output voltages (signals). In some embodiments, the three (3) analog output voltages from each plate component 110, 112 are then transmitted to an analog preamplifier board 170 in the base assembly 106 for preconditioning (i.e., signals $S_{FPO1}$-$S_{FPO6}$ in FIG. 12). The preamplifier board is used to increase the magnitudes of the transducer analog output voltages. After which, the analog force plate output signals $S_{APO1}$-$S_{APO6}$ are transmitted from the analog preamplifier 170 to the programmable logic controller (PLC) 172 of the base assembly 106. In the programmable logic controller (PLC) 172, analog force plate output signals $S_{APO1}$-$S_{APO6}$ are converted into forces, moments, centers of pressure (COP), and/or a center of gravity (COG) for the subject. Then, the forces, moments, centers of pressure (COP), subject center of gravity (COG), and/or sway angle for the subject computed by the programmable logic controller 172 are transmitted to the data acquisition/data processing device 104 (operator computing device 104) so that they can be utilized in reports displayed to an operator OP. Also, in yet another embodiment, the preamplifier board 170 additionally could be used to convert the analog voltage signals into digital voltage signals (i.e., the preamplifier board 170 could be provided with an analog-to-digital converter). In this embodiment, digital voltage signals would be transmitted to the programmable logic controller (PLC) 172 rather than analog voltage signals.

Figure 5:
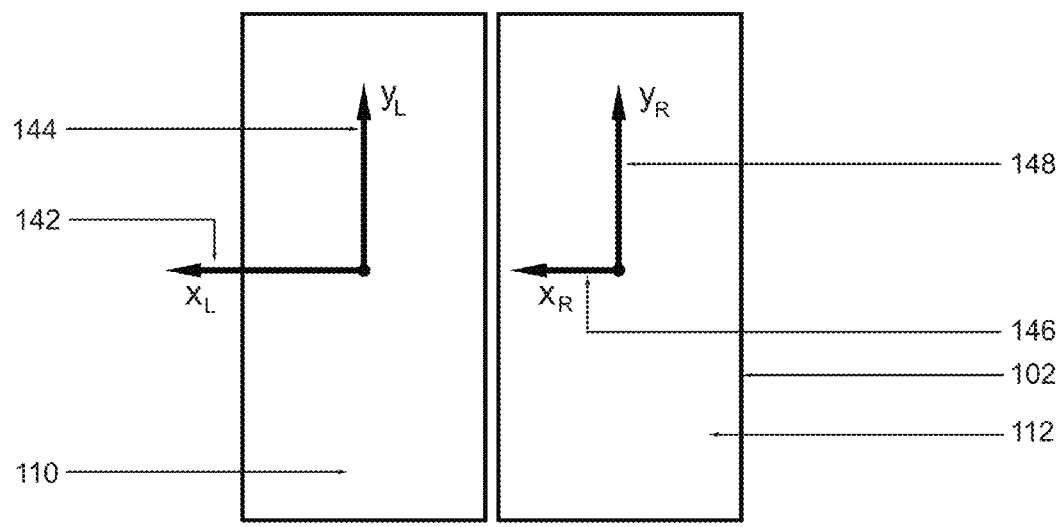
FIG. 5 is a diagrammatic top view of one measurement assembly used in the force measurement system with exemplary coordinate axes superimposed thereon, according to an embodiment of the invention, wherein the measurement assembly is in the form of a dual force plate.

When the programmable logic controller 172 receives the voltage signals $S_{ACO1}$-$S_{ACO6}$, it initially transforms the signals into output forces and/or moments by multiplying the voltage signals $S_{ACO1}$-$S_{ACO6}$ by a calibration matrix (e.g., $F_{Lz}$, $M_{Lx}$, $M_{Ly}$, $F_{Rz}$, $M_{Rx}$, $M_{Ry}$). After which, the center of pressure for each foot of the subject (i.e., the x and y coordinates of the point of application of the force applied to the measurement surface by each foot) are determined by the programmable logic controller 172. Referring to FIG. 5, which depicts a top view of the measurement assembly 102, it can be seen that the center of pressure coordinates ($x_{P_L}$, $y_{P_L}$) for the first plate component 110 are determined in accordance with x and y coordinate axes 142, 144. Similarly, the center of pressure coordinates ($x_{P_R}$, $y_{P_R}$) for the second plate component 112 are determined in accordance with x and y coordinate axes 146, 148. If the force transducer technology described in application Ser. No. 13/348,506 is employed, it is to be understood that the center of pressure coordinates ($x_{P_L}$, $y_{P_L}$, $x_{P_R}$, $x_{P_R}$) can be computed in the particular manner described in that application.

Figure 7:
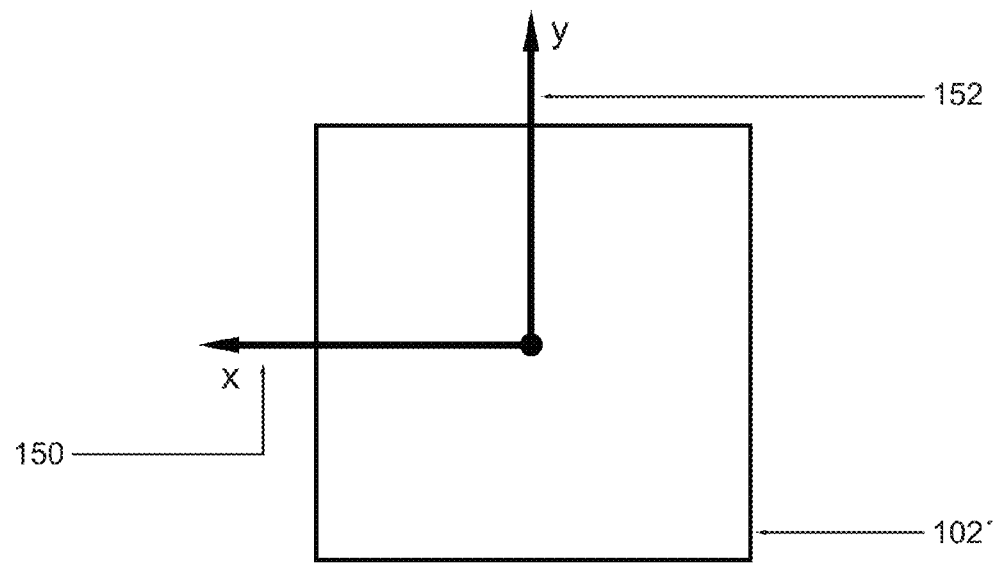
FIG. 7 is a diagrammatic top view of another measurement assembly used in the force measurement system with exemplary coordinate axes superimposed thereon, according to an embodiment of the invention, wherein the measurement assembly is in the form of a single force plate.

As explained above, rather than using a measurement assembly 102 having first and second plate components 110, 112, a force measurement assembly 102' in the form of a single force plate may be employed (see FIGS. 6 and 7, which illustrate a single force plate). As discussed hereinbefore, the single force plate comprises a single measurement surface on which both of a subject's feet are placed during testing. As such, rather than computing two sets of center of pressure coordinates (i.e., one for each foot of the subject), the embodiments employing the single force plate compute a single set of overall center of pressure coordinates ($x_P$, $y_P$) in accordance with x and y coordinate axes 150, 152.

In one exemplary embodiment, the programmable logic controller 172 in the base assembly 106 determines the vertical forces $F_{Lz}$, $F_{Rz}$ exerted on the surface of the first and second force plates by the feet of the subject and the center of pressure for each foot of the subject, while in another exemplary embodiment, the output forces of the data acquisition/data processing device 104 include all three (3) orthogonal components of the resultant forces acting on the two plate components 110, 112 (i.e., $F_{Lx}$, $F_{Ly}$, $F_{Lz}$, $F_{Rx}$, $F_{Ry}$, $F_{Rz}$) and all three (3) orthogonal components of the moments acting on the two plate components 110, 112 (i.e., $M_{Lx}$, $M_{Ly}$, $M_{Lz}$, $M_{Rx}$, $M_{Ry}$, $M_{Rz}$). In yet other embodiments of the invention, the output forces and moments of the data acquisition/data processing device 104 can be in the form of other forces and moments as well.

In the illustrated embodiment, the programmable logic controller 172 converts the computed center of pressure (COP) to a center of gravity (COG) for the subject using a Butterworth filter. For example, in one exemplary, non-limiting embodiment, a second-order Butterworth filter with a 0.75 Hz cutoff frequency is used. In addition, the programmable logic controller 172 also computes a sway angle for the subject using a corrected center of gravity (COG') value, wherein the center of gravity (COG) value is corrected to accommodate for the offset position of the subject relative to the origin of the coordinate axes (142, 144, 146, 148) of the force plate assembly 102. For example, the programmable logic controller 172 computes the sway angle for the subject in the following manner:

$$\theta = \sin^{-1}\left(\frac{COG'}{0.55\ h}\right) - 2.3° \quad (1)$$

where:

θ: sway angle of the subject;
COG': corrected center of gravity of the subject; and
h: height of the center of gravity of the subject.

Now, referring again to the block diagram of FIG. 12, the manner in which the motion of the force measurement assembly 102 is controlled will be explained. Initially, an operator OP inputs one or more motion commands at the operator computing device 104 (data acquisition/data processing device 104) by utilizing one of the user input devices 132, 134. Once, the one or more motion commands are processed by the operator computing device 104, the motion command signals are transmitted to the programmable logic controller 172. Then, after further processing by the programmable logic controller 172, the motion command signals are transmitted to the actuator control drive 174. Finally, the actuator control drive 174 transmits the direct-current (DC) motion command signals to the first and second actuator assemblies 158, 160 so that the force measurement assembly 102, and the subject disposed thereon, can be displaced in the desired manner. The actuator control drive 174 controls the position, velocity, and torque of each actuator motor.

In order to accurately control the motion of the force measurement assembly 102, a closed-loop feedback control routine may be utilized by the force measurement system 100. As shown in FIG. 12, the actuator control drive 174 receives the position, velocity, and torque of each actuator motor from the encoders provided as part of each actuator assembly 158, 160. Then, from the actuator control drive 174, the position, velocity, and torque of each actuator motor is transmitted to the programmable logic controller 172, wherein the feedback control of the first and second actuator assemblies 158, 160 is carried out. In addition, as illustrated in FIG. 12, the position, velocity, and torque of each actuator motor is transmitted from the programmable logic controller 172 to the operator computing device 104 so that it is capable of being used to characterize the movement of the subject on the force measurement assembly 102 (e.g., the motor positional data and/or torque can be used to compute the sway of the subject). Also, the rotational and translational positional data that is received from first and second actuator assemblies 158, 160 can be transmitted to the operator computing device 104.

Next, the electrical single-line diagram of FIG. 13, which schematically illustrates the power distribution system for the base assembly 106, will be explained. As shown in this figure, the building power supply is electrically coupled to an isolation transformer 176 (also refer to FIG. 3). In one exemplary embodiment, the isolation transformer 176 is a medical-grade isolation transformer that isolates the electrical system of the base assembly 106 from the building electrical system. The isolation transformer 176 greatly minimizes any leakage currents from the building electrical system, which could pose a potential safety hazard to a subject standing on the metallic base assembly 106. The primary winding of the isolation transformer 176 is electrically coupled to the building electrical system, whereas the secondary winding of isolation transformer 176 is electrically coupled to the programmable logic controller 172 (as schematically illustrated in FIG. 13).

Referring again to FIG. 13, it can be seen that the programmable logic controller 172 is electrically coupled to the actuator control drive 174 via an emergency stop (E-stop) switch 138. As explained above, in one embodiment, the emergency stop switch 138 is in the form of a red pushbutton that can be easily pressed by a user of the force measurement system 100 (e.g., a subject on the force measurement assembly 102 or an operator) in order to quasi-instantaneously stop the displacement of the force measurement assembly 102. Because the emergency stop switch 138 is designed to fail open, the emergency stop switch 138 is a fail-safe means of aborting the operations (e.g., the software operations) performed by the programmable logic controller 172. Thus, even if the programmable logic controller 172 fails, the emergency stop switch 138 will not fail, thereby cutting the power to the actuator control drive 174 so that the force measurement assembly 102 remains stationary (i.e., the brakes on the actuator assemblies 158, 160 will engage, and thus, prevent any intentional movement thereof). Also, in one embodiment, the emergency stop switch assembly 138 includes a reset button for re-enabling the operation of the actuator control drive 174 after it is has been shut down by the emergency stop switch.

Figure 13:
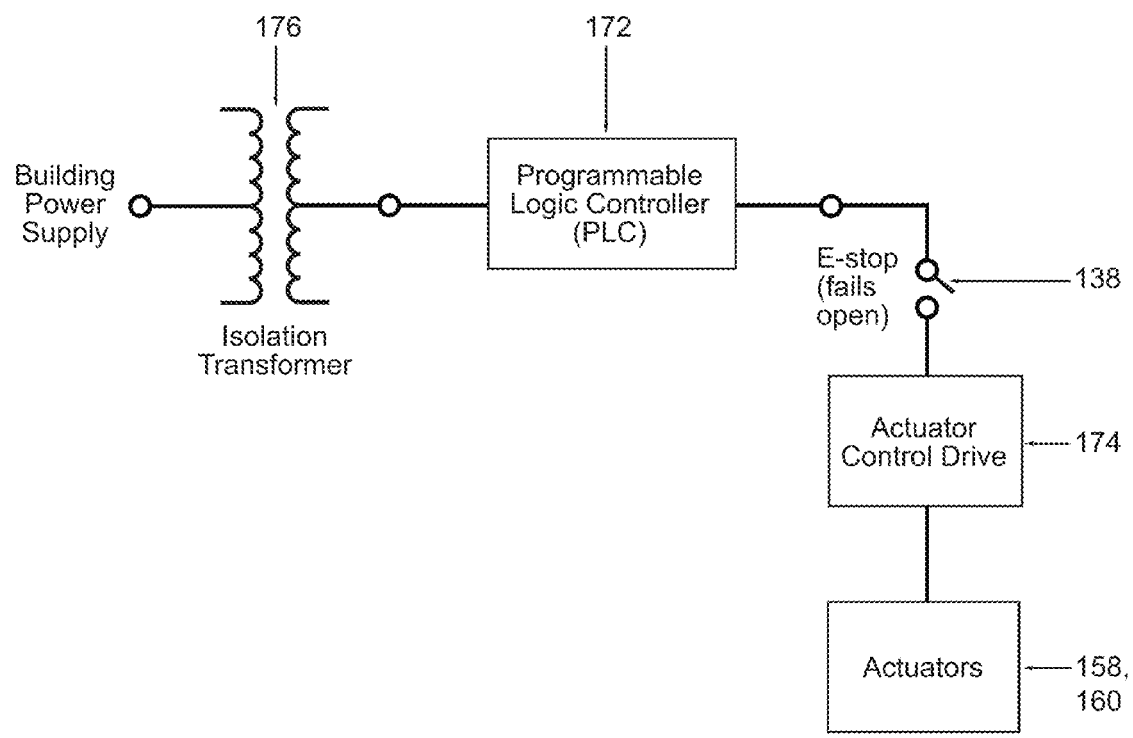
FIG. 13 is a single-line diagram of the base assembly electrical power system, according to an embodiment of the invention.

As shown in FIG. 13, the first and second actuator assemblies 158, 160 are powered by the actuator control drive 174. While not explicitly shown in FIG. 13, the electrical system of the base assembly 106 may further include a power entry module that includes a circuit breaker (e.g., a 20A circuit breaker) and a filter. Also, the electrical system of the base assembly 106 may additionally include an electromagnetic interference (EMI) filter that reduces electrical noise so as to meet the requirements of the Federal Communications Commission (FCC).

Now, specific functionality of the immersive virtual reality environment of the force measurement system 100 will be described in detail. It is to be understood that the aforedescribed functionality of the immersive virtual reality environment of the force measurement system 100 can be carried out by the data acquisition/data processing device 104 (i.e., the operator computing device) utilizing software, hardware, or a combination of both hardware and software. For example, the data acquisition/data processing device 104 can be specially programmed to carry out the functionality described hereinafter. In one embodiment of the invention, the computer program instructions necessary to carry out this functionality may be loaded directly onto an internal data storage device 104c of the data acquisition/data processing device 104 (e.g., on a hard drive thereof) and subsequently executed by the microprocessor 104a of the data acquisition/data processing device 104. Alternatively, these computer program instructions could be stored on a portable computer-readable medium (e.g., a flash drive, a floppy disk, a compact disk, etc.), and then subsequently loaded onto the data acquisition/data processing device 104 such that the instructions can be executed thereby. In one embodiment, these computer program instructions are embodied in the form of a virtual reality software program executed by the data acquisition/data processing device 104. In other embodiments, these computer program instructions could be embodied in the hardware of the data acquisition/data processing device 104, rather than in the software thereof. It is also possible for the computer program instructions to be embodied in a combination of both the hardware and the software.

As described above, in one or more embodiments of the invention, one or more virtual reality scenes are projected on the generally hemispherical projection screen 168 of the subject visual display device 107 so that the visual perception of a subject can be effectively altered during a test being performed using the force measurement system 100 (e.g., a balance test). In order to illustrate the principles of the invention, the immersive virtual reality environment of the force measurement system 100 will be described in conjunction with an exemplary balance assessment protocol, namely the Sensory Organization Test ("SOT"). Although, those of ordinary skill in the art will readily appreciate that the immersive virtual reality environment of the force measurement system 100 can be utilized with various other assessment protocols as well. For example, the force measurement system 100 could also include protocols, such as the Center of Gravity ("COG") Alignment test, the Adaption Test ("ADT"), the Limits of Stability ("LOS") test, the Weight Bearing Squat test, the Rhythmic Weight Shift test, and the Unilateral Stance test. In addition, the immersive virtual reality environment of the force measurement system 100 can be used with various forms of training, such as seated training, mobility training, closed chain training, weight shifting training, and quick training.

People maintain their upright posture and balance using inputs from somatosensory, vestibular and visual systems. In addition, individuals also rely upon inputs from their somatosensory, vestibular and visual systems to maintain balance when in other positions, such as seated and kneeling positions. During normal daily activity, where dynamic balance is to be maintained, other factors also matter. These factors are visual acuity, reaction time, and muscle strength. Visual acuity is important to see a potential danger. Reaction time and muscle strength are important to be able to recover from a potential fall. During the performance of the Sensory Organization Test ("SOT"), certain sensory inputs are taken away from the subject in order to determine which sensory systems are deficient or to determine if the subject is relying too much on one or more of the sensory systems. For example, the performance of the SOT protocol allows one to determine how much a subject is relying upon visual feedback for maintaining his or her balance.

Figure 14:
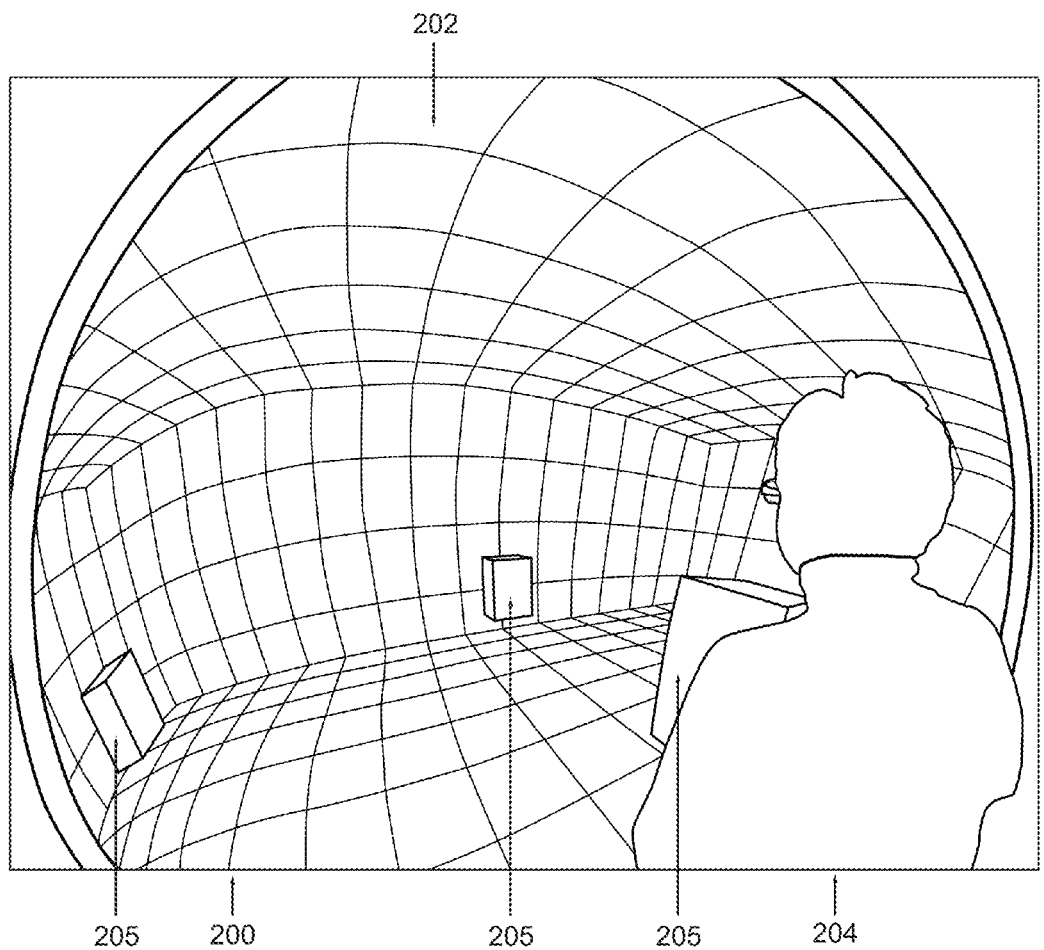
FIG. 14 is a first example of a virtual reality scene displayed on the subject visual display device of the force measurement system, according to an embodiment of the invention.

In one embodiment, the SOT protocol comprises six conditions under which a subject is tested (i.e., six test stages). In accordance with the first sensory condition, a subject simply stands in stationary, upright position on the force plate assembly 102 with his or her eyes open. During the first condition, a stationary virtual reality scene is projected on the generally hemispherical projection screen 168 of the subject visual display device 107, and the force plate assembly 102 is maintained in a stationary position. For example, the virtual reality scene displayed on the generally hemispherical projection screen 168 may comprise a checkerboard-type enclosure or room (e.g., see FIG. 14). In the illustrated embodiment, the virtual reality scene is in the form of a three-dimensional image, and the nature of the scene will remain consistent throughout the performance of the SOT protocol. As shown in the screen image 200 of FIG. 14, a subject 204 is disposed in an immersive virtual reality environment 202 comprising a three-dimensional checkerboard room. As shown in FIG. 14, the three-dimensional checkerboard room comprises a plurality of three-dimensional boxes or blocks 205 in order to give the subject 204 a frame of reference for perceiving the depth of the room (i.e., the boxes or blocks 205 enhance the depth perception of the subject 204 with regard to the virtual room).

In accordance with the second sensory condition of the SOT protocol, the subject is blindfolded so that he or she is unable to see the surrounding environment. Similar to the first condition, the force plate assembly 102 is maintained in a stationary position during the second condition of the SOT test. By blindfolding the subject, the second condition of the SOT effectively removes the visual feedback of the subject.

During the third condition of the SOT protocol, like the first and second conditions, the force plate assembly 102 remains in a stationary position. However, in accordance with the third sensory condition of the test, the virtual reality scene displayed on the generally hemispherical projection screen 168 is moved in sync with the sway angle of the subject disposed on the force plate assembly 102. For example, when the subject leans forward on the force plate assembly 102, the virtual reality scene displayed on the screen 168 is altered so as to appear to the subject to be inwardly displaced on the output screen 168. Conversely, when the subject leans backward on the force plate assembly 102, the virtual reality scene is adjusted so as to appear to the subject to be outwardly displaced on the screen 168. As in the first condition, the eyes of the subject remain open during the third condition of the SOT protocol.

In accordance with the fourth sensory condition of the SOT protocol, the force plate assembly 102 and the subject disposed thereon is displaced (e.g., rotated), while the eyes of the subject remain open. The force plate assembly 102 is displaced according to the measured sway angle of the subject (i.e., the rotation of the force plate assembly 102 is synchronized with the computed sway angle of the subject). During the fourth condition, similar to the first condition, a stationary virtual reality scene is projected on the generally hemispherical projection screen 168 of the subject visual display device 107.

During the fifth condition of the SOT protocol, like the second condition thereof, the subject is blindfolded so that he or she is unable to see the surrounding environment. However, unlike during the second condition, the force plate assembly 102 does not remain stationary, rather the force plate assembly 102 and the subject disposed thereon is displaced (e.g., rotated). As for the fourth condition, the force plate assembly 102 is displaced according to the measured sway angle of the subject (i.e., the rotation of the force plate assembly 102 is synchronized with the computed the sway angle of the subject). As was described above for the second condition of SOT protocol, by blindfolding the subject, the fifth condition of the SOT test effectively removes the visual feedback of the subject.

Lastly, during the sixth sensory condition of the SOT protocol, like the fourth and fifth conditions, the force plate assembly 102 and the subject disposed thereon is displaced (e.g., rotated). Although, in accordance with the sixth sensory condition of the test, the virtual reality scene displayed on the generally hemispherical projection screen 168 is also moved in sync with the sway angle of the subject disposed on the force plate assembly 102. As previously described for the fourth and fifth conditions, the displacement of the force plate assembly 102 is governed by the measured sway angle of the subject (i.e., the rotation of the force plate assembly 102 is synchronized with the computed the sway angle of the subject). In an exemplary embodiment, when the subject is forwardly displaced on the force plate assembly 102 during the sixth condition of the SOT protocol, the virtual reality scene displayed on the screen 168 is altered so as to appear to the subject to be inwardly displaced on the output screen 168. Conversely, when the subject is rearwardly displaced on the force plate assembly 102, the virtual reality scene is adjusted so as to appear to the subject to be outwardly displaced on the screen 168. As in the fourth condition, the eyes of the subject remain open during the sixth condition of the SOT protocol.

Figure 16:
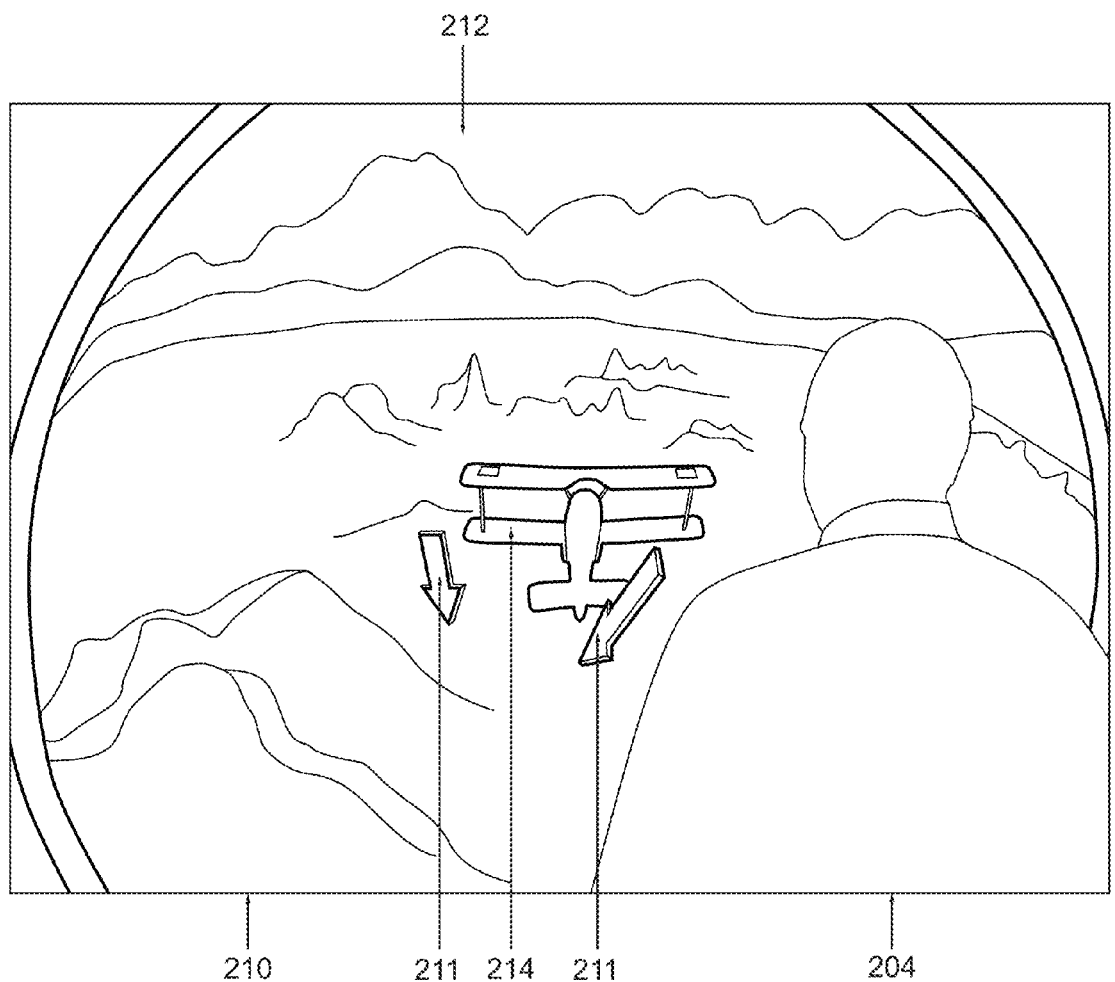
FIG. 16 is a first variation of an interactive game displayed on the subject visual display device of the force measurement system, according to an embodiment of the invention.
Figure 17:
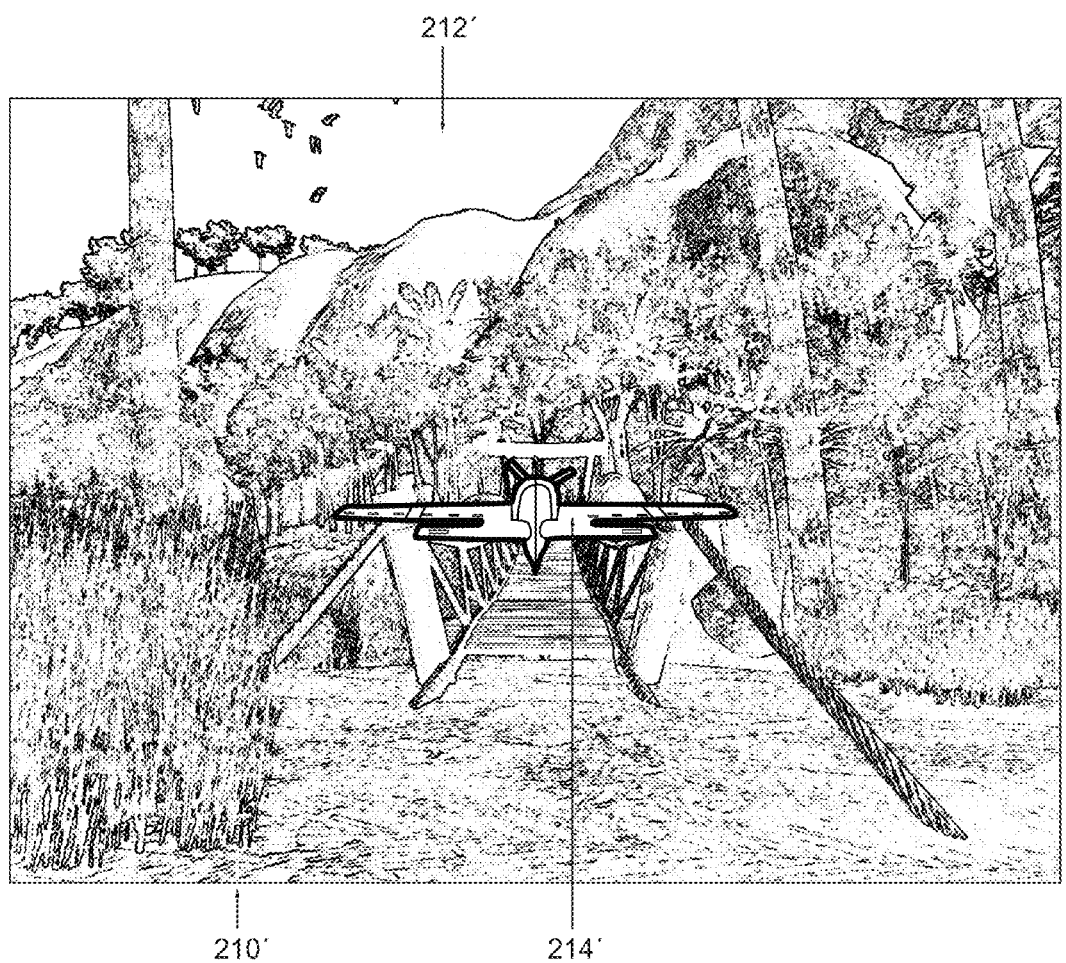
FIG. 17 is a second variation of an interactive game displayed on the subject visual display device of the force measurement system, according to an embodiment of the invention, wherein a game element is in a first position.
Figure 18:
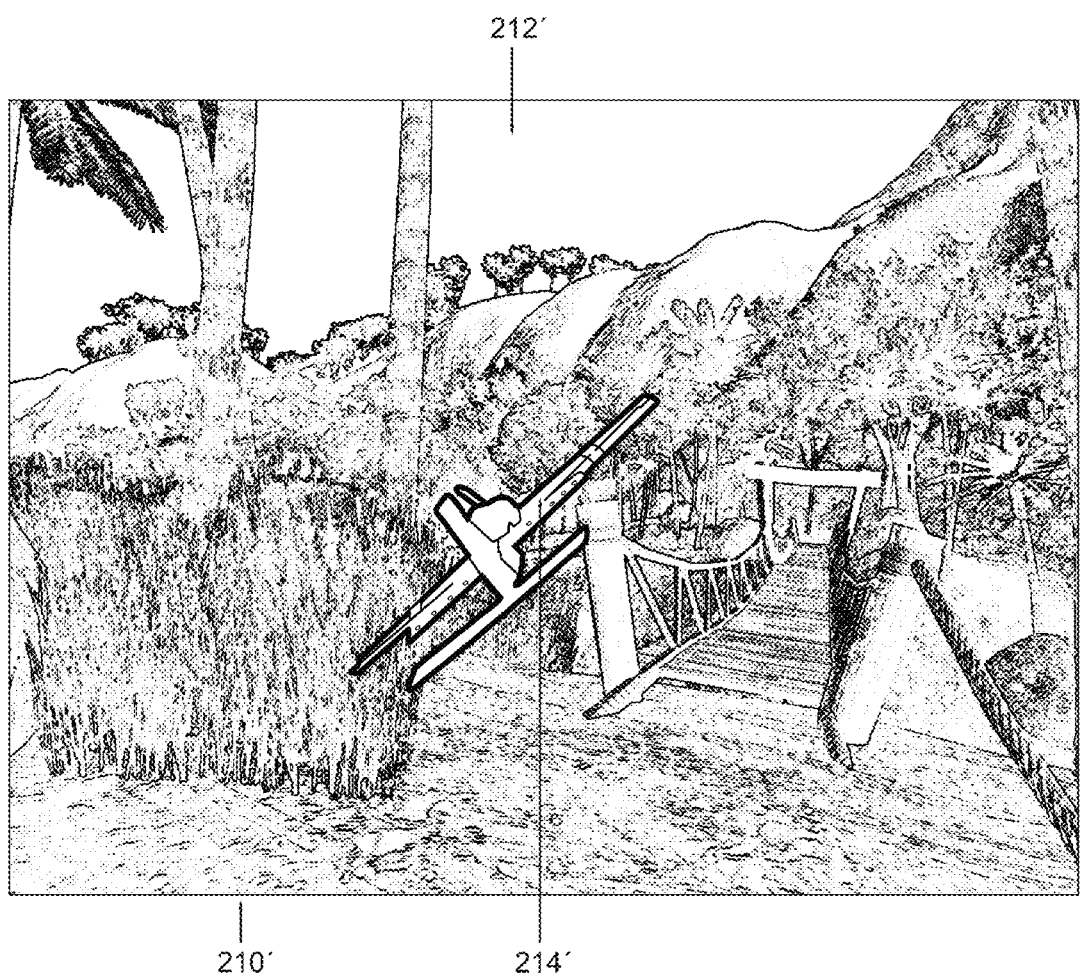
FIG. 18 is a second variation of an interactive game displayed on the subject visual display device of the force measurement system, according to an embodiment of the invention, wherein the game element is in a second position.
Figure 19:
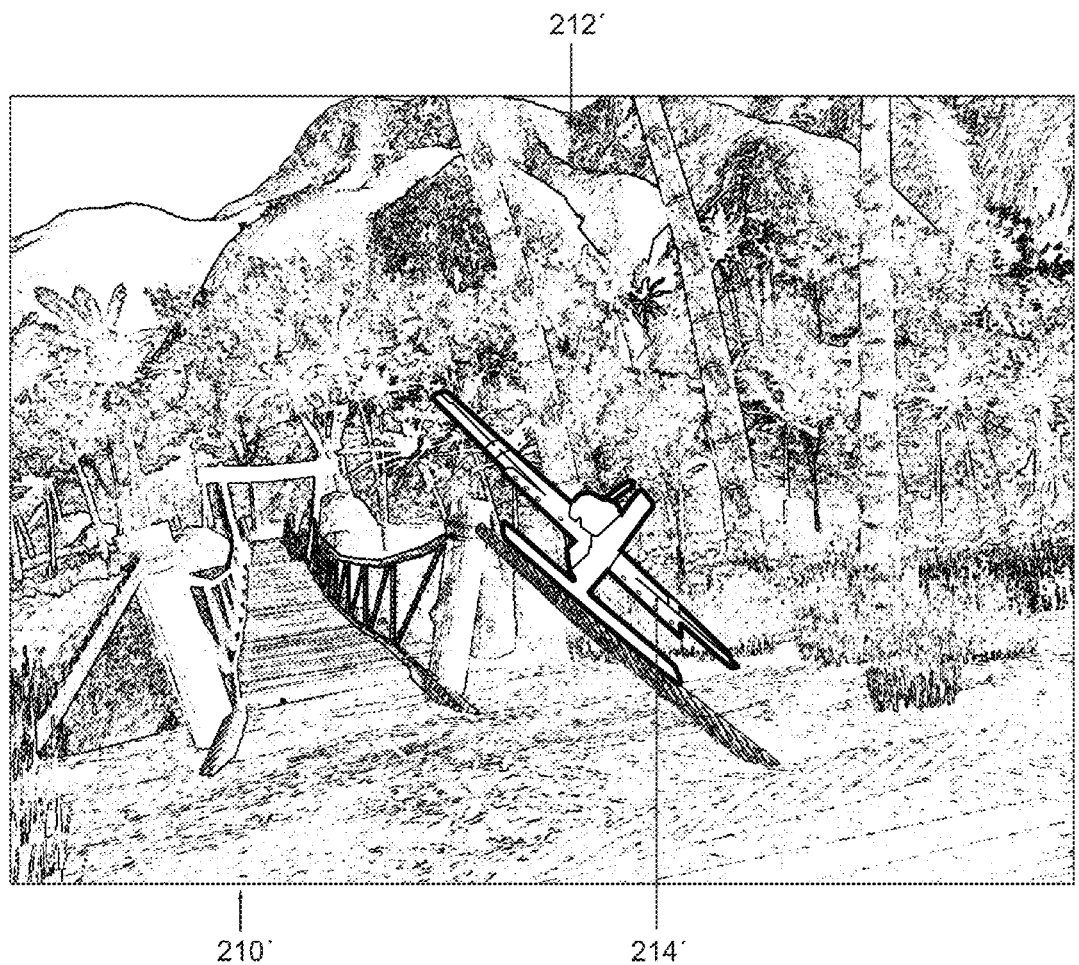
FIG. 19 is a second variation of an interactive game displayed on the subject visual display device of the force measurement system, according to an embodiment of the invention, wherein the game element is in a third position.
Figure 20:
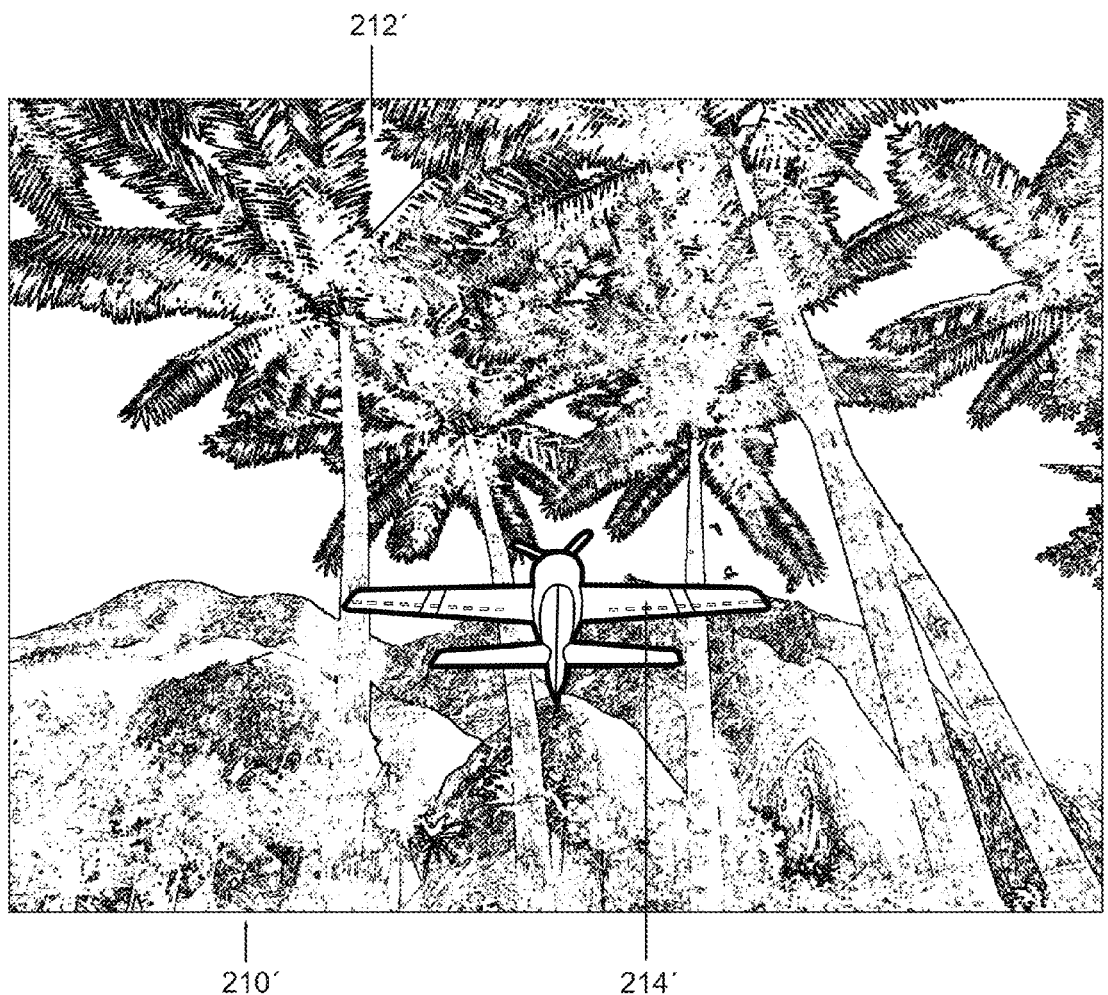
FIG. 20 is a second variation of an interactive game displayed on the subject visual display device of the force measurement system, according to an embodiment of the invention, wherein the game element is in a fourth position.
Figure 21:
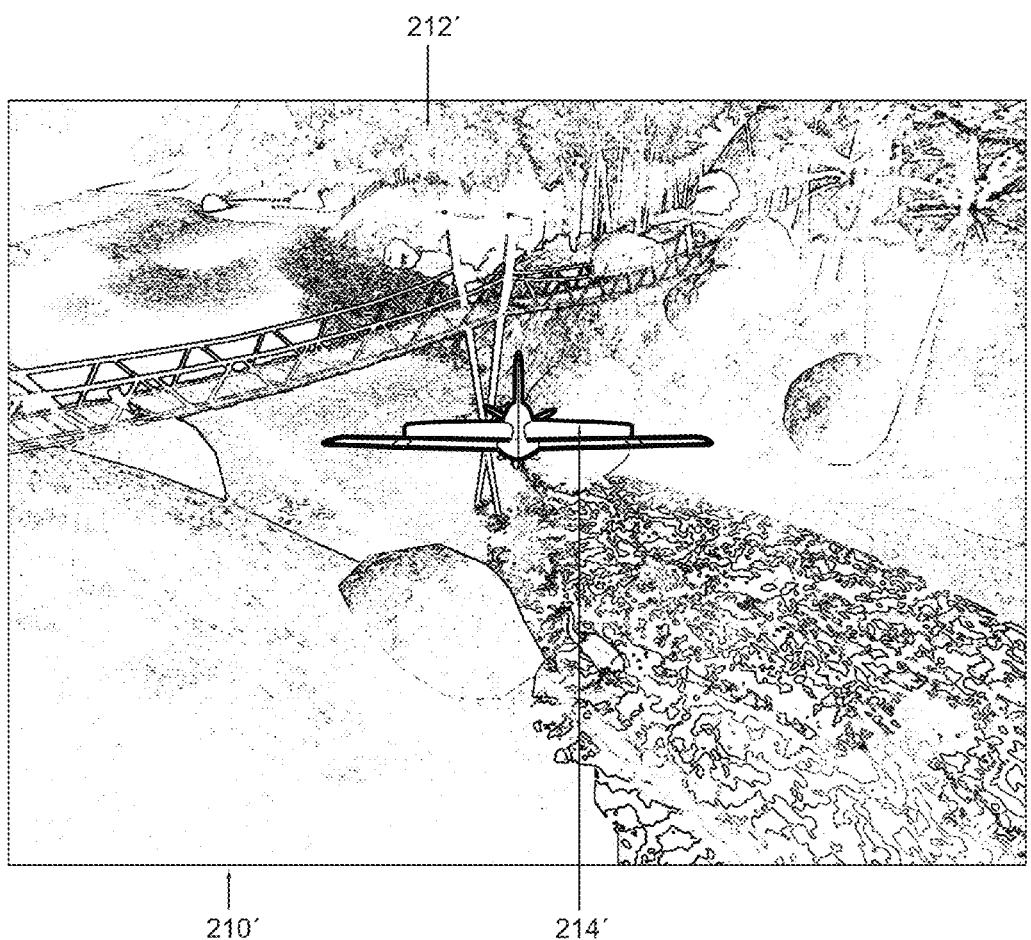
FIG. 21 is a second variation of an interactive game displayed on the subject visual display device of the force measurement system, according to an embodiment of the invention, wherein the game element is in a fifth position.

In further embodiments of the invention, the data acquisition/data processing device 104 is configured to control the movement of a game element of an interactive game displayed on the immersive subject visual display device 107 by using one or more numerical values determined from the output signals of the force transducers associated with the force measurement assembly 102. Referring to screen images 210, 210' illustrated in FIGS. 16-21, it can be seen that the game element may comprise, for example, an airplane 214, 214' that can be controlled in a virtual reality environment 212, 212'. With particular reference to FIG. 16, because a subject 204 is disposed within the confines of the generally hemispherical projection screen 168 while playing the interactive game, he or she is completely immersed in the virtual reality environment 212. FIG. 16 illustrates a first variation of this interactive game, whereas FIGS. 17-21 illustrate a second variation of this interactive game (e.g., each variation of the game uses a different airplane 214, 214' and different scenery). Although FIGS. 17-21 depict generally planar images, rather than a concave image projected on a generally hemispherical screen 168 as shown in FIG. 16, it is to be understood that the second variation of the interactive game (FIGS. 17-21) is equally capable of being utilized on a screen that at least partially surrounds a subject (e.g., a generally hemispherical projection screen 168). In the first variation of the interactive airplane game illustrated in FIG. 16, arrows 211 can be provided in order to guide the subject 204 towards a target in the game. For example, in the first variation of the interactive game, the subject 204 may be instructed to fly the airplane 214 through one or more targets (e.g., rings or hoops) in the virtual reality environment 212. When the airplane is flown off course by the subject 204, arrows 211 can be used to guide the subject 204 back to the general vicinity of the one or more targets.

In an illustrative embodiment, the one or more numerical values determined from the output signals of the force transducers associated with the force measurement assembly 102 comprise the center of pressure coordinates ($x_P$, $y_P$) computed from the ground reaction forces exerted on the force plate assembly 102 by the subject. For example, with reference to the force plate coordinate axes 150, 152 of FIG. 7, when a subject leans to the left on the force measurement assembly 102 (i.e., when the x-coordinate $x_P$ of the center of pressure is positive), the airplane 214' in the interactive game is displaced to the left (see e.g., FIG. 18). Conversely, when a subject leans to the right on the force measurement assembly 102 (i.e., when the x-coordinate $x_P$ of the center of pressure is negative in FIG. 7), the airplane 214' in the interactive game is displaced to the right (see e.g., FIG. 19). When a subject leans forward on the force measurement assembly 102 (i.e., when the y-coordinate $y_P$ of the center of pressure is positive in FIG. 7), the altitude of the airplane 214' is increased (see e.g., FIG. 20). Conversely, when a subject leans backward on the force measurement assembly 102 (i.e., when the y-coordinate $y_P$ of the center of pressure is negative in FIG. 7), the altitude of the airplane 214' is decreased (see e.g., FIG. 21).

In other further embodiments of the invention, the force measurement system 100 described herein is used for assessing the visual flow of a particular subject, and at least in cases, the impact of a subject's visual flow on the vestibular systems. In one or more exemplary embodiments, the assessment of visual flow is concerned with determining how well a subject's eyes are capable of tracking a moving object.

In still further embodiments, the force measurement system 100 described herein is used for balance sensory isolation, namely selectively isolating or eliminating one or more pathways of reference (i.e., proprioceptive, visual, and vestibular). As such, it is possible to isolate the particular deficiencies of a subject. For example, the elderly tend to rely too heavily upon visual feedback in maintaining their balance. Advantageously, tests performed using the force measurement system 100 described herein could reveal an elderly person's heavy reliance upon his or her visual inputs.

Figure 15:
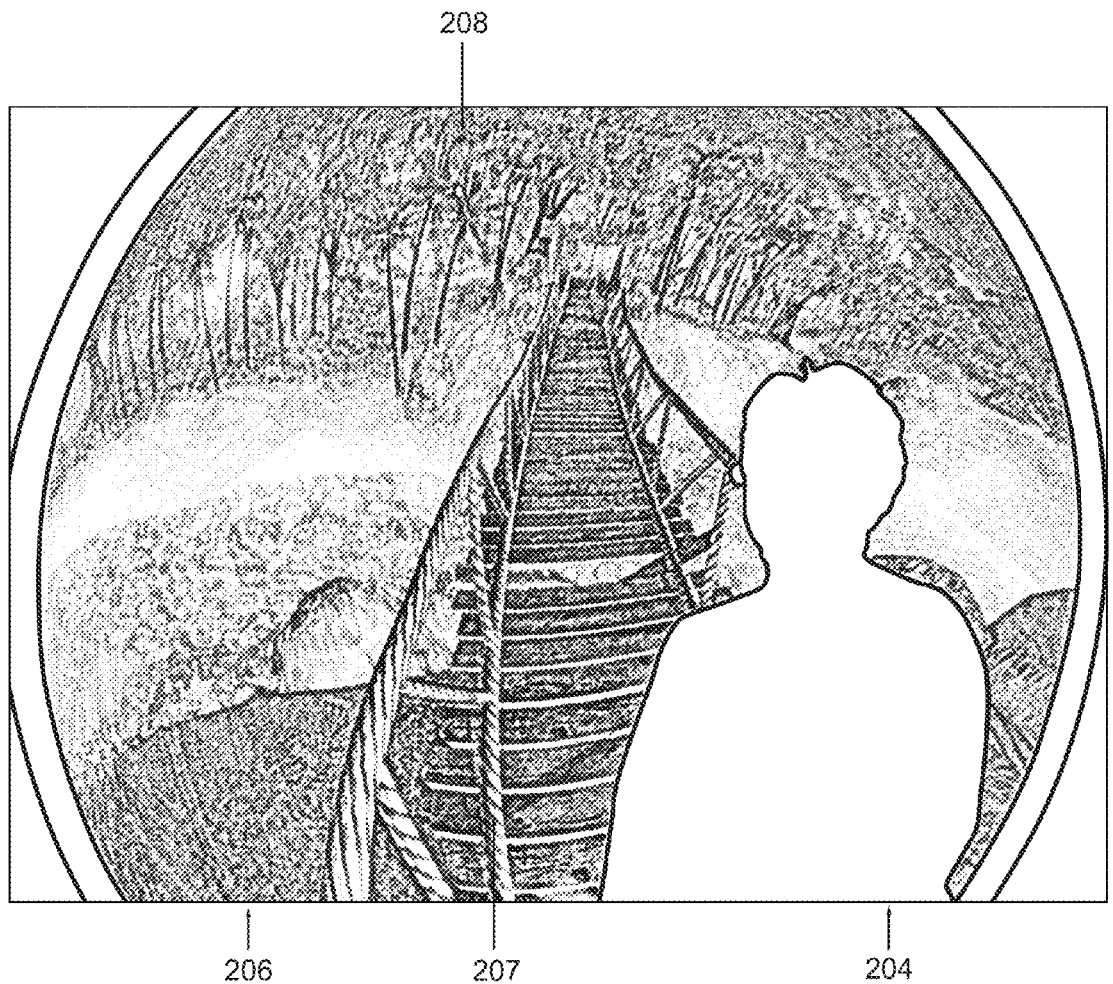
FIG. 15 is a second example of a virtual reality scene displayed on the subject visual display device of the force measurement system, according to an embodiment of the invention.

Although the invention has been shown and described with respect to a certain embodiment or embodiments, it is apparent that this invention can be embodied in many different forms and that many other modifications and variations are possible without departing from the spirit and scope of this invention. In particular, while an interactive airplane game is described in the embodiment described above, those of ordinary skill in the art will readily appreciate that the invention is not so limited. For example, as illustrated in the screen image 206 of FIG. 15, the immersive virtual reality environment 208 could alternatively comprise a scenario wherein the subject 204 is walking along a bridge 207. In addition, any other suitable game and/or protocol involving a virtual reality scenario can be used in conjunction with the aforedescribed force measurement system. As such, the claimed invention may encompass any such suitable game and/or protocol.

Moreover, while reference is made throughout this disclosure to, for example, "one embodiment" or a "further embodiment", it is to be understood that some or all aspects of these various embodiments may be readily combined with another as part of an overall embodiment of the invention.

Furthermore, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A force measurement system having a displaceable force measurement assembly, the force measurement system comprising:
    a force measurement assembly configured to receive a subject, the force measurement assembly including:
        a top surface for receiving at least one portion of the body of the subject; and
        a plurality of load cells, each of the plurality of load cells configured to sense one or more measured quantities and output one or more signals that are representative of forces and/or moments being applied to the top surface of the force measurement assembly by the subject;
    at least one actuator operatively coupled to the force measurement assembly, the at least one actuator configured to displace the force measurement assembly;
    a base assembly having a stationary portion and a displaceable portion, the force measurement assembly forming a part of the displaceable portion of the base assembly, the at least one actuator configured to rotate the force measurement assembly relative to the stationary portion of the base assembly about a transverse rotational axis disposed above the top surface of the force measurement assembly;
    at least one visual display device having an output screen configured to at least partially circumscribe three sides of a torso of the subject, the at least one visual display device configured to display one or more virtual reality scenes on the output screen so that the scenes are viewable by the subject, wherein the one or more virtual reality scenes are configured to create a simulated environment for the subject, wherein opposed sides of the output screen of the at least one visual display device inwardly converge towards the displaceable portion of the base assembly; and
    one or more data processing devices operatively coupled to the force measurement assembly, the at least one actuator, and the at least one visual display device, the one or more data processing devices configured to receive the one or more signals that are representative of the forces and/or moments being applied to the top surface of the force measurement assembly by the subject, and to convert the one or more signals into output forces and/or moments, the one or more data processing devices further configured to selectively displace the force measurement assembly using the at least one actuator.

2. The force measurement system according to claim 1, wherein the at least one actuator is disposed above the top surface of the force measurement assembly.

3. The force measurement system according to claim 1, wherein the at least one actuator comprises a first actuator configured to rotate the force measurement assembly about the transverse rotational axis and a second actuator configured to translate the displaceable portion of the base assembly that includes the force measurement assembly.

4. The force measurement system according to claim 1, wherein a width of the output screen of the at least one visual display device is greater than a width of the force measurement assembly, but not substantially greater than a width of the base assembly.

5. The force measurement system according to claim 1, wherein the base assembly and the force measurement assembly each have a width measured in a direction generally parallel to the coronal plane of the subject and a length measured in a direction generally parallel to the sagittal plane of the subject, wherein a width of the output screen of the at least one visual display device is greater than the width of the force measurement assembly and less than approximately 1.5 times the width of the base assembly, and wherein a depth of the output screen of the at least one visual display device is greater than the length of the force measurement assembly and less than the length of the base assembly.

6. The force measurement system according to claim 1, wherein the one or more data processing devices adjust the one or more virtual reality scenes on the output screen of the at least one visual display device in accordance with a computed sway angle for the subject, the sway angle being computed as a function of the output forces and/or moments.

7. The force measurement system according to claim 1, wherein the one or more data processing devices adjust the one or more virtual reality scenes on the output screen of the at least one visual display device in accordance with the selected displacement of the force measurement assembly.

8. The force measurement system according to claim 1, wherein the output screen of the at least one visual display device engages enough of the peripheral vision of a subject such that the subject becomes immersed in the simulated environment.

9. The force measurement system according to claim 8, wherein a bottom portion of the output screen of the at least one visual display comprises a cutout configured to receive a portion of the body of the subject therein.

10. The force measurement system according to claim 1, wherein the at least one visual display comprises a projector, a convexly shaped mirror, and a concavely shaped projection screen, wherein the projector is configured to project an image onto the convexly shaped mirror, and the convexly shaped mirror is configured to project the image onto the concavely shaped projection screen.

11. The force measurement system according to claim 10, wherein the concavely shaped projection screen is generally hemispherical in shape, and wherein the convexly shaped mirror is disposed near a top of the concavely shaped projection screen.

12. The force measurement system according to claim 11, wherein the top of the concavely shaped projection screen comprises a cutout for accommodating a light beam of the projector.

13. The force measurement system according to claim 1, wherein the one or more data processing devices include a programmable logic controller configured to provide real-time control of the at least one actuator via an actuator control drive.

14. The force measurement system according to claim 13, wherein the programmable logic controller is configured to: (i) convert the one or more signals that are representative of the forces and/or moments being applied to the top surface of the force measurement assembly by the subject into output forces and/or moments, (ii) compute center of pressure coordinates for the applied forces and/or compute a center of gravity value for the subject using the output forces and/or moments, and (iii) transmit the computed center of pressure coordinates and/or the computed center of gravity value to a computing device operatively coupled to the programmable logic controller.

15. A method for testing a subject disposed on a displaceable force measurement assembly, the method comprising the steps of:
  providing a force measurement assembly configured to receive a subject, the force measurement assembly including:
    a top surface for receiving at least one portion of the body of the subject; and
    at least one force transducer, the at least one force transducer configured to sense one or more measured quantities and output one or more signals that are representative of forces and/or moments being applied to the top surface of the force measurement assembly by the subject;
  providing at least one actuator operatively coupled to the force measurement assembly, the at least one actuator configured to displace the force measurement assembly;
  providing a base assembly having a stationary portion and a displaceable portion, the force measurement assembly forming a part of the displaceable portion of the base assembly, the at least one actuator configured to rotate the force measurement assembly relative to the stationary portion of the base assembly about a transverse rotational axis disposed above the top surface of the force measurement assembly;
  providing at least one visual display device having an output screen configured to at least partially circumscribe three sides of a torso of the subject, the at least one visual display device configured to display one or more virtual reality scenes on the output screen so that the scenes are viewable by the subject, wherein opposed sides of the output screen of the at least one visual display device inwardly converge towards the displaceable portion of the base assembly;
  providing one or more data processing devices operatively coupled to the force measurement assembly, the at least one actuator, and the at least one visual display device, the one or more data processing devices configured to receive the one or more signals that are representative of the forces and/or moments being applied to the top surface of the force measurement assembly by the subject and to convert the one or more signals into output forces and/or moments, and the one or more data processing devices configured to selectively displace the force measurement assembly using the at least one actuator;

positioning the subject on the top surface of the force measurement assembly and at least partially within the output screen of the at least one visual display device such that the output screen at least partially circumscribes three sides of the torso of the subject;

selectively displacing the displaceable portion of the base assembly, the force measurement assembly, and the subject disposed thereon relative to the stationary portion of the base assembly using the at least one actuator, wherein selectively displacing the displaceable portion of the base assembly includes rotating the force measurement assembly about the transverse rotational axis disposed above the top surface of the force measurement assembly;

sensing, by utilizing the at least one force transducer, one or more measured quantities that are representative of forces and/or moments being applied to the top surface of the force measurement assembly by the subject and outputting one or more signals representative thereof;

converting, by using the one or more data processing devices, the one or more signals that are representative of the forces and/or moments being applied to the top surface of the force measurement assembly by the subject into output forces and/or moments; and displaying one or more virtual reality scenes to the subject utilizing the output screen of the at least one visual display device, the one or more virtual reality scenes creating a simulated environment for the subject.

16. The method according to claim 15, further comprising the steps of:
  positioning the subject in a substantially stationary position on the force measurement assembly; and
  generating, by using the one or more data processing devices, one or more virtual reality scenes in the form of one or more two-dimensional images or one or more three-dimensional images that appear to be displaced inwardly on the output screen of the at least one visual display device.

17. The method according to claim 15, further comprising the step of:
  generating, by using the one or more data processing devices, one or more virtual reality scenes in the form of one or more substantially stationary two-dimensional images or three-dimensional images on the output screen of the at least one visual display device while displacing the force measurement assembly and the subject disposed thereon using the at least one actuator.

18. The method according to claim 15, further comprising the step of:
  generating, by using the one or more data processing devices, one or more virtual reality scenes in the form of one or more two-dimensional images or one or more three-dimensional images that appear to be displaced inwardly on the output screen of the at least one visual display device while displacing the force measurement assembly and the subject disposed thereon using the at least one actuator.

19. A force measurement system having a displaceable force measurement assembly, the force measurement system comprising:
  a force measurement assembly configured to receive a subject, the force measurement assembly including:
    a top surface for receiving at least one portion of the body of the subject; and
    at least one force transducer, the at least one force transducer configured to sense one or more measured quantities and output one or more signals that are representative of forces and/or moments being applied to the top surface of the force measurement assembly by the subject;
  at least one first actuator operatively coupled to the force measurement assembly, the at least one first actuator configured to rotate the force measurement assembly about a transverse rotational axis disposed above the top surface of the force measurement assembly, the at least one first actuator disposed above the top surface of the force measurement assembly;
  at least one second actuator operatively coupled to the force measurement assembly, the at least one second actuator configured to translate the force measurement assembly, the at least one second actuator disposed below the top surface of the force measurement assembly;
  a base assembly having a stationary portion and a displaceable portion, the force measurement assembly forming a part of the displaceable portion of the base assembly, the at least one first actuator and the at least one second actuator configured to displace the force measurement assembly relative to the stationary portion of the base assembly;
  one or more data processing devices operatively coupled to the force measurement assembly, the at least one first actuator, and the at least one second actuator, the one or more data processing devices configured to receive the one or more signals that are representative of the forces and/or moments being applied to the top surface of the force measurement assembly by the subject and to convert the one or more signals into output forces and/or moments, the one or more data processing devices configured to selectively displace the force measurement assembly using the at least one first actuator and the at least one second actuator; and
  at least one visual display device having an output screen configured to at least partially circumscribe three sides of a torso of the subject, the at least one visual display device configured to display one or more virtual reality scenes on the output screen so that the scenes are viewable by the subject, wherein the one or more virtual reality scenes are configured to create a simulated environment for the subject, wherein opposed sides of the output screen of the at least one visual display device inwardly converge towards the displaceable portion of the base assembly.

20. The force measurement system according to claim 19, wherein the first and second actuators are disposed in the base assembly, the base assembly having a step height measured from a ground surface to an upper surface thereof, wherein a placement of the at least one first actuator above the top surface of the force measurement assembly results in a reduction of the step height of the base assembly.

21. The force measurement system according to claim 19, wherein the one or more data processing devices include a programmable logic controller configured to provide real-time control of the at least one first actuator and the at least one second actuator via an actuator control drive.

* * * * *